(12) United States Patent
Bucholz

(10) Patent No.: US 6,374,135 B1
(45) Date of Patent: *Apr. 16, 2002

(54) SYSTEM FOR INDICATING THE POSITION OF A SURGICAL PROBE WITHIN A HEAD ON AN IMAGE OF THE HEAD

(75) Inventor: Richard D. Bucholz, St. Louis, MO (US)

(73) Assignee: Saint Louis University, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/457,699

(22) Filed: Dec. 9, 1999

Related U.S. Application Data

(63) Continuation of application No. 09/243,804, filed on Feb. 3, 1999, which is a continuation of application No. 08/477,561, filed on Jun. 7, 1995, now Pat. No. 5,891,034, which is a continuation of application No. 08/053,076, filed on Apr. 26, 1993, now abandoned, which is a continuation-in-part of application No. 07/858,980, filed on May 15, 1992, now abandoned, which is a continuation-in-part of application No. 07/909,097, filed on Jul. 2, 1992, now Pat. No. 5,383, 454, which is a continuation-in-part of application No. PCT/US91/07745, filed on Oct. 17, 1991, which is a continuation-in-part of application No. 07/600,753, filed on Oct. 19, 1990, now abandoned.

(51) Int. Cl.[7] .................................................. A61B 5/00
(52) U.S. Cl. .................. 600/427; 600/429; 606/130
(58) Field of Search ................................ 600/426, 427, 600/429, 411, 414, 417; 606/130

(56) References Cited

U.S. PATENT DOCUMENTS

| 3,821,469 A | 6/1974 | Whetstone et al. |
| D233,265 S | 10/1974 | Walchel |
| 3,868,565 A | 2/1975 | Kuipers |

(List continued on next page.)

FOREIGN PATENT DOCUMENTS

| DE | 2534516 A1 | 2/1976 |
| DE | 2534516 | 2/1976 |
| DE | 2852949 | 6/1980 |

(List continued on next page.)

OTHER PUBLICATIONS

Adams, L., et al., "Orientation Aid For Head and Neck Sugeons," *Innov. Tech. Biol. Med.*, vol. 13, No. 4, 1992, pp. 410–424.

Adams, L. et al., "Medical Imaging. Computer-Assisted Surgery," *IEEE Computer Graphics & Applications*, 1990, pp. 43–51.

Afshar, Farhad, et al., "A three-dimensional reconstruction of the human brain stem," *J. Neurosurg.*, vol. 57, No. 4, Oct. 1982, pp. 491–495.

(List continued on next page.)

*Primary Examiner*—Ruth S. Smith
(74) *Attorney, Agent, or Firm*—Senniger, Powers, Leavitt & Roedel

(57) ABSTRACT

A system for determining a position of a probe relative to an object such as a head of a body of a patient. The head includes a surface such as a forehead having a contour. Cross sectional images of the head are scanned and stored as a function of the forehead contour. If the forehead contour does not appear in the scan images, then the position of the forehead contour relative to the scan images is determined with an optical scanner and a ring. During surgery, the optical scanner also determines the position of the forehead relative to the ring. An array for receiving radiation emitted from the probe and from the ring generates signals indicating the position of the tip of the probe relative to the ring. A stereotactic imaging system generates and displays an image of the head corresponding to the measured position of the tip of the probe. The system may also display scan images from different scanning technologies which scan images correspond to the same position in the head.

43 Claims, 14 Drawing Sheets

U.S. PATENT DOCUMENTS

| | | |
|---|---|---|
| 3,871,133 A | 3/1975 | Mushabac |
| 3,963,028 A | 6/1976 | Cooley et al. |
| 3,971,133 A | 7/1976 | Mushabac |
| 3,983,474 A | 9/1976 | Kuipers |
| 4,058,114 A | 11/1977 | Soldner |
| 4,068,156 A | 1/1978 | Johnson et al. |
| 4,068,556 A | 1/1978 | Foley |
| 4,071,456 A | 1/1978 | McGee et al. |
| 4,117,337 A | 9/1978 | Staats |
| 4,182,312 A | 1/1980 | Mushabac |
| 4,209,254 A | 6/1980 | Reymond |
| 4,262,306 A | 4/1981 | Renner |
| 4,341,220 A | 7/1982 | Perry |
| 4,358,856 A | 11/1982 | Stivender et al. |
| 4,407,298 A | 10/1983 | Lentz et al. |
| 4,419,012 A | 12/1983 | Stephenson et al. |
| 4,457,311 A | 7/1984 | Sorenson et al. |
| 4,465,069 A | 8/1984 | Barbier et al. |
| 4,473,074 A | 9/1984 | Vassiliadis |
| 4,506,676 A | 3/1985 | Duska |
| 4,543,959 A | 10/1985 | Sepponen |
| 4,553,285 A | 11/1985 | Sachs et al. |
| 4,571,834 A | 2/1986 | Fraser et al. |
| 4,583,538 A | 4/1986 | Onik et al. |
| 4,585,350 A | 4/1986 | Pryer et al. |
| 4,592,352 A | 6/1986 | Patil |
| 4,602,622 A | 7/1986 | Bär et al. |
| 4,608,977 A | 9/1986 | Brown |
| 4,638,798 A | 1/1987 | Sheldon et al. |
| 4,645,343 A | 2/1987 | Stockdale et al. |
| 4,649,504 A | 3/1987 | Krouglicof et al. |
| 4,651,732 A | 3/1987 | Frederick |
| 4,659,971 A | 4/1987 | Suzuki et al. |
| 4,660,970 A | 4/1987 | Ferrano |
| 4,672,306 A | 6/1987 | Thong |
| 4,673,352 A | 6/1987 | Hansen |
| 4,674,057 A | 6/1987 | Caughman et al. |
| D291,246 S | 8/1987 | Lower |
| 4,686,997 A | 8/1987 | Oloff et al. |
| 4,698,777 A | 10/1987 | Toyoda et al. |
| 4,701,047 A | 10/1987 | Eibert et al. |
| 4,701,049 A | 10/1987 | Beckmann et al. |
| 4,705,401 A | 11/1987 | Addleman |
| 4,706,665 A | 11/1987 | Gouda |
| 4,709,156 A | 11/1987 | Murphy et al. |
| 4,721,384 A | 1/1988 | Dietrich et al. |
| 4,721,388 A | 1/1988 | Takagi et al. |
| 4,722,056 A | 1/1988 | Roberts et al. |
| 4,723,544 A | 2/1988 | Moore et al. |
| 4,727,565 A | 2/1988 | Ericson |
| 4,733,316 A | 3/1988 | Oishi et al. |
| 4,733,661 A | 3/1988 | Palestrant |
| 4,733,662 A | 3/1988 | DeSatnick et al. |
| 4,733,969 A | 3/1988 | Case et al. |
| 4,737,032 A | 4/1988 | Addleman et al. |
| 4,737,921 A | 4/1988 | Goldwasser et al. |
| 4,742,815 A | 5/1988 | Ninan et al. |
| 4,743,770 A | 5/1988 | Lee |
| 4,743,771 A | 5/1988 | Sacks et al. |
| 4,745,290 A | 5/1988 | Frankel et al. |
| 4,750,487 A | 6/1988 | Zanetti |
| 4,753,128 A | 6/1988 | Bartlett et al. |
| 4,753,528 A | 6/1988 | Hines |
| 4,761,072 A | 8/1988 | Pryor |
| 4,762,016 A | 8/1988 | Stoughton et al. |
| 4,764,015 A | 8/1988 | Bieringer et al. |
| 4,764,016 A | 8/1988 | Johanasson |
| 4,767,934 A | 8/1988 | Stauffer |
| 4,771,787 A | 9/1988 | Wurster et al. |
| 4,779,212 A | 10/1988 | Levy |
| 4,782,239 A | 11/1988 | Hirose et al. |
| 4,788,481 A | 11/1988 | Niwa |
| D298,862 S | 12/1988 | Tharp et al. |
| D298,863 S | 12/1988 | Tharp et al. |
| D299,070 S | 12/1988 | Tharp et al. |
| 4,791,934 A | 12/1988 | Brunnett |
| 4,793,355 A | 12/1988 | Crum et al. |
| 4,794,262 A | 12/1988 | Sato et al. |
| 4,803,645 A | 2/1989 | Ohtomo et al. |
| 4,805,615 A | 2/1989 | Carol |
| 4,809,694 A | 3/1989 | Ferrara |
| 4,821,200 A | 4/1989 | Öberg |
| 4,821,206 A | 4/1989 | Arora |
| 4,822,163 A | 4/1989 | Schmidt |
| 4,825,091 A | 4/1989 | Breyer et al. |
| 4,829,373 A | 5/1989 | Leberl et al. |
| 4,835,710 A | 5/1989 | Schnelle et al. |
| 4,836,778 A | 6/1989 | Baumrind et al. |
| 4,837,669 A | 6/1989 | Tharp et al. |
| 4,841,967 A | 6/1989 | Chang et al. |
| 4,875,478 A | 10/1989 | Chen |
| 4,896,673 A | 1/1990 | Rose et al. |
| 4,923,459 A | 5/1990 | Nambu |
| 4,931,056 A | 6/1990 | Ghajar et al. |
| 4,933,843 A | 6/1990 | Scheller et al. |
| 4,943,296 A | 7/1990 | Funakubo et al. |
| 4,945,914 A | 8/1990 | Allen |
| 4,954,043 A | 9/1990 | Yoshida et al. |
| 4,955,891 A | 9/1990 | Carol |
| 4,991,579 A | 2/1991 | Allen |
| 5,002,687 A | 3/1991 | Roberts et al. |
| 5,005,142 A | 4/1991 | Lipchak et al. |
| 5,016,639 A | 5/1991 | Allen |
| 5,017,139 A | 5/1991 | Mushabac |
| 5,027,818 A | 7/1991 | Bova et al. |
| 5,039,867 A | 8/1991 | Nishihara et al. |
| 5,047,036 A | 9/1991 | Koutrouvelis |
| 5,050,608 A | 9/1991 | Watanabe et al. |
| 5,059,789 A | 10/1991 | Salcudean et al. |
| 5,078,140 A | 1/1992 | Kwoh |
| 5,078,142 A | 1/1992 | Siczek et al. |
| 5,079,699 A | 1/1992 | Tuy et al. |
| 5,080,662 A | 1/1992 | Paul |
| 5,086,401 A | 2/1992 | Glassman et al. |
| 5,094,241 A | 3/1992 | Allen |
| 5,097,839 A | 3/1992 | Allen |
| 5,099,846 A | 3/1992 | Hardy |
| 5,107,839 A | 4/1992 | Houdek et al. |
| 5,119,817 A | 6/1992 | Allen |
| 5,142,930 A | 9/1992 | Allen et al. |
| 5,161,676 A | 11/1992 | Gunther et al. |
| 5,163,430 A | 11/1992 | Carol |
| 5,178,164 A | 1/1993 | Allen |
| 5,186,174 A | 2/1993 | Schlöndorff et al. |
| 5,193,106 A | 3/1993 | DeSena |
| 5,197,476 A | 3/1993 | Nowacki et al. |
| 5,198,877 A | 3/1993 | Schulz |
| 5,222,499 A | 6/1993 | Allen et al. |
| 5,224,049 A | 6/1993 | Mushabac |
| 5,230,338 A | 7/1993 | Allen et al. |
| 5,249,581 A | 10/1993 | Horbal et al. |
| 5,251,127 A | 10/1993 | Raab |
| 5,257,998 A | 11/1993 | Ota et al. |
| 5,261,404 A | 11/1993 | Mick et al. |
| 5,279,309 A | 1/1994 | Taylor et al. |
| 5,291,889 A | 3/1994 | Kenet et al. |
| 5,295,200 A | 3/1994 | Boyer |
| 5,295,483 A | 3/1994 | Nowacki et al. |
| 5,299,288 A | 3/1994 | Glassman et al. |
| 5,305,091 A | 4/1994 | Gelbart et al. |
| 5,305,203 A | 4/1994 | Raab |

| | | |
|---|---|---|
| 5,309,913 A | 5/1994 | Kormos et al. |
| 5,332,971 A | 7/1994 | Aubert |
| D349,573 S | 8/1994 | Bookwalter et al. |
| 5,355,129 A | 10/1994 | Baumann |
| 5,357,953 A | 10/1994 | Merrick et al. |
| 5,359,417 A | 10/1994 | Müller |
| 5,368,030 A | 11/1994 | Zinreich et al. |
| D353,668 S | 12/1994 | Banks et al. |
| 5,371,778 A | 12/1994 | Yanof et al. |
| 5,383,454 A | 1/1995 | Bucholz |
| 5,389,101 A | 2/1995 | Heilbrun et al. |
| 5,398,684 A | 3/1995 | Hardy |
| 5,399,146 A | 3/1995 | Nowacki et al. |
| 5,399,951 A | 3/1995 | Lavallee et al. |
| D357,534 S | 4/1995 | Hayes |
| D359,557 S | 6/1995 | Hayes |
| 5,483,961 A | 1/1996 | Kelly et al. |
| 5,494,034 A | 2/1996 | Schlöndorff et al. |
| 5,515,160 A | 5/1996 | Schulz |
| 5,517,990 A | 5/1996 | Kalfas et al. |
| 5,531,520 A | 7/1996 | Grimson et al. |
| 5,603,318 A | 2/1997 | Heilbrun et al. |
| 5,622,170 A | 4/1997 | Schulz |
| 5,638,819 A | 6/1997 | Manwaring et al. |
| 5,662,111 A | 9/1997 | Cosman |
| 5,682,886 A | 11/1997 | Delp et al. |
| 5,732,703 A | 3/1998 | Kalfas |
| 5,748,767 A | 5/1998 | Raab |
| 5,776,064 A | 7/1998 | Kalfas |
| 5,836,954 A | 11/1998 | Heilbrun et al. |
| 5,848,967 A | 12/1998 | Cosman |
| 5,868,675 A | 2/1999 | Henrion et al. |
| 5,891,034 A * | 4/1999 | Bucholz .................... 600/426 |
| 5,920,395 A | 7/1999 | Schulz |
| 6,076,008 A * | 6/2000 | Bucholz .................... 600/427 |

FOREIGN PATENT DOCUMENTS

| | | |
|---|---|---|
| DE | 3205085 A1 | 9/1983 |
| DE | 3508730 A1 | 9/1986 |
| DE | 8701668.0 | 5/1987 |
| DE | 37 17 871 C2 | 12/1988 |
| DE | 3831278 A1 | 3/1989 |
| DE | 38 38 011 A1 | 7/1989 |
| DE | 3904595 C1 | 4/1990 |
| DE | 39 02 249 | 8/1990 |
| DE | 3205915 | 9/1993 |
| EP | 0 018 166 | 10/1980 |
| EP | 0 062 941 | 10/1982 |
| EP | 0 155 857 | 9/1985 |
| EP | 0 207 452 | 1/1987 |
| EP | 0 359 773 B1 | 5/1988 |
| EP | 0 322 363 | 6/1989 |
| EP | 0 326 768 A2 | 8/1989 |
| EP | 0 427 358 A1 | 5/1991 |
| FR | 359773 B1 | 2/1979 |
| FR | 2 417 970 | 10/1979 |
| GB | 2094590 | 9/1982 |
| JP | 62-000327 | 1/1987 |
| WO | WO 88/09151 | 12/1988 |
| WO | WO 90/05494 | 5/1990 |
| WO | WO 91/07726 | 5/1991 |
| WO | WO 92/06645 | 4/1992 |
| WO | WO 92/10439 | 11/1992 |
| WO | WO 96/11624 | 4/1996 |

OTHER PUBLICATIONS

Apuzzo, M.L.J. et al., "Computed Tomographic Guidance Stereotaxis in the Management of Intracranial Mass Lesions," *Neurosurgery*, vol. 12, No. 3, 1983, pp. 277–285.

Arun, K.S., et al., "Transactions on Pattern Analysis and Machine Intelligence," *IEEE*, vol. PAMI–9, No. 5, 1987, pp. 698–770.

Awwad, Eric E., et al., "Post–Traumatic Spinal Synovial Cyst with Spondylolysis CT Features," *Journal of Computer Assisted Tomography*, vol. 13, No. 2, pp. 334–337, Mar./Apr. 1989.

Awwad, Eric E., et al., "MR Imaging of Lumbar Juxtaarticular Cysts," *Journal of Computer Assisted Tomography*, vol. 14, No. 3, pp. 415–417, May/Jun. 1990.

Bajcsy, Ruzena, et al., "Computerized Anatomy Atlas of the Human Brain," Proceedings of the Second Annual Conference & Exhibition of The National Computer Graphics Association, Inc., Jun. 14–18, 1981, pp. 435–441.

Barnett, G.H., et al., "Armless Wand for Accurate Frameless Stereotactic Surgical Localization," Poster #1119, *Scientific Program*, 1992 Annual Meeting, American Association of Neurological Surgeons, San Francisco, CA, Apr. 11–16, 1992, pp. 284–285.

Batnitzky, Solomon, M.D., et al., "Three–Dimensional Computer Reconstructions of Brain Lesions from Surface Contours Provided by Computed Tomography: A Prospectus," *Neurosurgery*, vol. 11, No. 1, Jul. 1982, pp. 73–84.

Bergström, Mats, et al., "Stereotaxic Computed Tomography," *Am. J. Roentgenol.* 127:167–170, 1976, pp. 167–170.

Birg, W., et al., "A Computer Programme System for Stereotactic Neurosurgery," *Acta Neurochirurgica Suppl.*, 24, 1977, 99–108.

Boëthius, J., et al., "Stereotaxic computerized tomography with a GE 8800 scanner," *J. Neurosurg*, vol. 52, Jun. 1980, pp. 794–800.

Boëthius, J., et al., "Stereotactic Biopsies and Computer Tomography in Gliomas," *Acta Neurochirurgica*, vol. 40, Fasc. 3–4, 1978, pp. 223–232.

Brown, Russell A., M.D., "A computerized tomography–computer graphics approach to stereotaxic localization," *J. Neurosurg*, vol. 50, No. 6, 1979, pp. 715–720.

Bucholz, Richard D., et al., "Armless Wand for Accurate Frameless Stereotactic Surgical Localization," American Association of Neurological Surgeons 1992 Annual Meeting, pp. 284–285, poster 1120.

Bucholz, Richard D., et al., "Halo Vest Versus Spinal Fusion for cervical injury: evidence from an outcome study," *J. Neurosurg.*, vol. 70, No. 6, pp. 884–892, Jun. 1989.

Bucholz, R.D., et al., "Use of an Intraoperative Optical Digitizer in a System for Free–Hand Stereotactic Surgery," Poster #1120, *Scientific Program*, 1992 Annual Meeting, American Association of Neurological Surgeons, San Francisco, CA, Apr. 11–16, 1992, pp. 284–285.

Bucholz, Richard D., et al., "Intraoperative Localization Using a Three Dimensional Optical Digitizer," *Proceedings of Clinical Applications of Modern Imaging Technology*, SPIE, vol. 1894, The International Society of Optical Engineering, pp. 312–322, Jan. 17–19, 1993.

Bullard, D.E., et al., "C.T.–Guided Stereotactic Biopsies Using a Modified Frame and Gildenberg Techniques," *Neurology, Neurosurgery, and Psychiatry*, vol. 47, pp. 590–595, 1984.

BYTE Magazine, "3–D Digitizer Captures the World" (Oct. 1990), p. 43.

Champleboux, et al., "Accurate Calibration of Cameras and Range Imaging Sensors: the NPBS Method," 1992, 6 pages.

Champleboux, "Utilisation De Fonctions Splines Pour La Mise Au Point d'Un Capteur Tridimension Sans Contact," Theses, Docteur de L'Univerite' Joseph Fourie Grenoble 1, Jul. 1991.

Cinquin, et al., "Computer Assisted Medical Interventions," The 1$^{st}$ Workshop on Domestic Robotics—The 2$^{nd}$ Workshop on Medical & Healthcare Robotics, Sep. 5–7, 1989, pp. 63–65.

Cinquin, et al., "IGOR: Image Guided Operating Robot, Methodology, Applications," IEEE EMBS, Paris, 1992 pp. 1–2.

Colchester et al., "Information Processing in Medical Imaging," Lecture Notes in Computer Science, Jul. 1991, pp. 51–58.

Dever, Bill and S. James Zinreich, M.D., "OR role seen for 3–D imaging," *Radiology Today*, 2 pages, Feb. 1991.

Foley, Kevin T., et al., "Image–Guided Intraoperative Spinal Localization," *Intraoperative Neuroprotection*, Chapter 19, pp. 325–340, 1996.

Foley, J.D., et al., "Geometrical Transformations," *Fundamentals of Interactive Computer Graphics, The Systems Programming Series*, Addison–Wesley Publishing Company, 1982, pp. 245–266.

Friets et al., "A Frameless Sterotaxic Operating Microscope for Neurosurgery", IEEE Transactions on Biomedical Engineering, vol. 36, No. 6 (Jun. 1989), pp. 608, 613–617.

Galloway, Jr., Robert L., et al.,"Interactive Image–Guided Neurosurgery," *IEEE Transactions on Biomedical Engineering*, vol. 39, No. 12, pp. 1226–1231, Dec. 1992.

Gildenberg, Philip L., M.D., et al., "Calculation of Stereotactic Coordinates from the Computed Tomographic Scan," *Neurosurgery*, vol. 10, No. 5, May 1982, pp. 580–586.

Glaser, Edmund M. et al., "The Image–Combining Computer Microscope—an Interactive Instrument of Morphometry of the Nervous System," *Journal of Neuroscience Methods*, vol. 8, pp. 17–32, 1983.

Gleason, Curtis A., Ph.D., et al., "Sterotactic Localization (with Computerized Tomographic Scanning), Biopsy, and Radiofrequency Treatment of Deep Brain Lesions," *Neurosurgery*, vol. 2, No. 3, 1978, pp. 217–222.

Gomez, Camilo R., et al., "Transcranial Doppler Ultrasound Following Closed Head Injury: Vasospasm or Vasoparalysis?," *Surg. Neurol.*, vol. 35, No. 1, pp. 30–35, Jan. 1991.

Gonzalez, Rafael C., et al., "Digital Image Fundamentals," *Digital Imaging Processing Second Edition*, Addison–Wesley Publishing Company, 1987, pp. 52–54.

Gouda, Kasim I., M.D., et al., "New frame for stereotaxic surgery," *J. Neurosurg*, vol. 53, Aug. 1980, pp. 256–259.

Hahn, Joseph F., M.D., et al., "Needle Biopsy of Intracranial Lesions Guided by Computerized Tomography," *Neurosurgery*, vol. 5, No. 1, 1979, pp. 11–15.

Hanson, Gayle, "Robots Roll into Operating Rooms," *Insight*, Apr. 8, 1991, pp. 44–45.

Hatch, John F., "Reference–Display System for the Integration of CT Scanning and the Operating Microscope," Dartmouth College, Oct. 1984, entire thesis.

Hatch, J.F., et al., "Reference–Display System for the Integration of CT Scanning and the Operating Microscope," Proceedings of the Eleventh Annual Northeast Bioengineering Conference, Mar. 14–15, 1985, *IEEE* 1985, pp. 252–254.

Heilbrun, M. Peter, et al., "Preliminary Experience with a Brown–Roberts–Wells (BRW) Computerized Tomography Stereotaxic Guidance System," *J. Neurosurg.*, vol. 59, pp. 217–222, Aug. 1983.

Heilbrun, M. Peter, et. al., "Stereotactic Localization and Guidance Using a Machine Vision Technique," *Stereotactic and Functional Surgery* (reprint), vol. 58, 1992, pp. 94–98.

Hinck, M.D., Vincent C., et al., "A precise technique for craniotomy localization using computerized tomography," *J. Neurosurgery*, vol. 54, No. 3, Mar. 1981, pp. 416–418.

Hoerenz, Peter, "The Operating Microscope, I., Optical Principles, Illumination Systems, and Support Systems," *Journal of Microsurgery*, vol. 1, No. 5, Mar.–Apr. 1980, pp. 364–369.

Holman, B. Leonard, et al., Computer–Assisted Superimposition of Magnetic Resonance and High–Resolution Technetium–99–m–HMPAO and Thallium–201 SPECT Images of the Brain, *The Journal of Nuclear Medicine*, vol. 32, No. 8, Aug. 1991, pp. 1478–1484.

Holman, B. Leonard, et al., "Correlation of projection radiographs in radiation therapy using open curve segments and points," *Med. Phys*, 19 (2), Mar./Apr. 1992, pp. 329–334.

Horner, M.D., Neil B., et al., "A Comparison of CT–Stereotaxic Brain Biopsy Techniques," *Investigative Radiology*, vol. 19, Sep.–Oct. 1984, pp. 367–373.

Hounsfield, G.N., "Computerized transverse axial scanning (tomography): Part 1., Description of System," *British Journal of Radiology*, vol. 46, 1973, pp. 1016–1022.

Jacques, Skip, M.D., et al., "Computerized three–dimensional stereotaxic removal of small central nervous system lesions in patients," *J. Neurosurg*, vol. 53, No. 6, Dec. 1980, pp. 816–820.

Jacques, Skip, M.D., et al., "A Computerized Microstereotactic Method to Approach, 3–Dimensionally Reconstruct, Remove and Adjuvantly Treat Small CNS Lesions," *Appl. Neurophysiology* 43:176–182, 1980.

Kato, et al., "A Frameless, Armless Navigational System for Computer Assisted Neurosurgery" 74 *J. Neurosurg*, 845–49, 1991.

Kaufman, Howard H., M.D., "New Head–positioning System for Use with Computed Tomographic Scanning," *Neurosurgery*, vol. 7, No. 2, Aug. 1980, pp. 147–149.

Kelly, Patrick J., M.D., et al. "A Microstereotactic Approach to Deep–seated Arteriovenous Malformations," *Surgical Neurology*, vol. 17, No. 4, Apr. 1982, pp. 260–262.

Kelly, Partick J., M.D., et al., "Computer–Assisted Stereotaxic Laser Resection of Intra–Axial Brain Neoplasma," *J. Neurosurg.*, vol. 64, Mar. 1976, pp. 427–439.

Kelly, M.D., Patrick J., et al., "A Stereotactic Approach to Deep–Seated Central Nervous System Neoplasms Using the Carbon Dioxide Laser," *Surgical Neurology*, vol. 15, No. 5, May 1981, pp. 331–334.

Kelly, Patrick J., et al., "Stereotactic CT Scanning for the Biopsy of Intracranial Lesions and Functional Neurosurgery," *Applied Neurophysiology*, vol. 46, Dec. 1983, pp. 193–199.

Kelly, P.J., et al., "Precision Resection of Intra–Axial CNS Lesions by CT–Based Stereotactic Craniotomy and Computer Monitored $CO_2$ Laser," *Acta Neurochirurgica*, vol. 68, Fasc. 1–2, 1983, pp. 1–9.

Kosugi, Yukio, et al., "An Articulated Neurosurgical Navigation System Using MRI and CT Images," *IEEE Transaction on Biomedical Engineering*, vol. 35, No. 2, Feb. 1988, pp. 147–152.

Krybus, W. et al., "Navigation Support for Surgery by Means of Optical Position Detection," *Proceedings of CAR '91*, pp. 362–366.

Kwoh, Yik San, et al.: A Robot with Improved Absolute Positions Accuracy for CT Guided Stereotactic Brain Surgery—IEEE Transactions on Biomedical Engineering, vol. 35, No. 2, Feb. 1988, pp. 153–160.

Lavalee, et al., "Computer Assisted Interventionist Imaging: The Instance of Stereotactic Brain Surgery," *Medinfo*, 1989, pp. 613–617.

Lavalee, et al., "Computer Assisted Medical Interventions," NATO ASI 1990, pp. 301–312, vol. F60.

Lavalee, et al., "Ponction Assistee Par Ordinateur" ("Computer Assisted Puncture"), *afcet INRIA*, Nov. 1987, pp. 439–449.

Lavalee, S., et al., "Matching 3–D Smooth Surfaces with Their 2–D Projections using 3–D Distance Maps," SPIE, vol. 1570, *Geometric Methods in Computer Vision*, (1991), pp. 322–336.

Lavalee, "A New System for Computer Assisted Neurosurgery," *IEEE Engineering in Medicine & Biology Society 11th Annual International Conference*, 1989.

Leksell, L., et al., "Stereotaxis and Tomography, A Technical Note," *Acta Neurochirurgica*, vol. 52, Fasc–1–2, 1980, pp. 1–7.

Lavalee, et al., "Computer Assisted Driving of a Needle into the Brain," *Computer Assisted Radiology*, 1989, pp. 416–420.

Levin, D., et al., "Multimodality 3–D View of the Brain Created from MRI and PET Scans," *SMRI 1989: Seventh Annual Meeting Program and Abstracts*, vol. 7, Supplement 1, p. 89.

Levin, David N., et al., "The Brain: Integrated Three–dimensional Display of MR and PET Images," *Radiology*, Sep. 1989, vol. 172, No. 3, pp. 783–789.

Levinthal, Robert, M.D., et al., "Technique for Accurate Localization with the CT Scanner," *Bulletin of the Los Angeles Neurological Societies*, vol. 41, No. 1, Jan. 1976, pp. 6–8.

Lunsford, L. Dade, M.D., "Innovations in Stereotactic Technique Coupled with Computerized Tomography," *Contemporary Neurosurgery*, 1982, pp. 1–6.

Mackay, Alexander R., M.D., et al., "Computed Tomography–directed Stereotaxy for Biopsy and Interstitial Irradiation of Brain Tumors: Technical Note," *Neurosurgery*, vol. 11, No. 1, 1982, pp. 38–42.

Maroon, Joseph C., M.D., et al., "Intracranial biopsy assisted by computerized tomography," *J. Neurosurg.*, vol. 46, No. 6, Jun. 1977, pp. 740–744.

Mazier, et al., "Computer Assisted Interventionist Imaging: Application to the Vertebral Column Surgery," IEEE, vol. 12, No. 1, 1990, pp. 430–431.

Mazier, et al., "Computer Assisted Vertebral Column Surgery: application to the Spinal Pedicle Fixation," *Innov. Tech. Biol. Med.*, vol. 11, No. 5, 1990, pp. 559–565.

Mesqui, F., et al., "Real–Time, Noninvasive Recording and Three–Dimensional Display of the Functional Movements of an Arbitrary Mandible Point", *Proceedings*, vol. 602, *Biostereometrics '85*, Dec. 3–6, 1985, Cannes, France, SPIE, vol. 602, pp. 77–84.

Mosges, Ralph, et al., "A New Imaging Method for Intraoperative Therapy Control in Skull–Base Surgery" (1988).

Mundinger, F., et al., "Computer–Assisted Stereotactic Brain Operations by Means Including Computerized Axial Tomography," *Applied Neurophysiology*, vol. 41, No. 1–4, 1978, pp. 169–182.

Mundinger, F., et al., "Treatment of Small Cerebral Gliomas with CT–Aided Stereotaxic Curietherapy," *Neuroradiology*, vol. 16, 1978, pp. 564–567.

Norman, David, M.D., et al., "Localization with the EMI Scanner," *The American Journal of Roentgenology, Radium Therapy and Nuclear Medicine*, vol. 125, No. 4, Dec. 1975, pp. 961–964.

O'Leary, M.D., Daniel H., et al., "Localization of vertex lesions seen on CT scan," *J. Neurosurg*, vol. 49, No. 1, Jul. 1978, pp. 71–74.

Ohbuchi, R., et al., "Incremental Volume Reconstruction and Rendering for 3D Ultrasound Imaging," SPIE vol. 1808, Visualization in Biomedical Computing, pp. 312–323, Oct. 9, 1992.

Patil, Arun–Angelo, M.D., "Computed Tomography Plane of the Target Approach in Computed Tomographic Stereotaxis," *Neurosurgery*, vol. 15, No. 3, Sep. 1984, pp. 410–414.

Paul, et al., "Development of a Surgical Robot for Cementless Total Hip Arthroplasty," *Clinical Orthopaedics*, No. 285, Dec. 1992, pp. 57–66.

Pelizzari, C.A., et al., "Interactive 3D Patient–Image Registration," *Information Processing in Medical Imaging*, pp. 132–141, Jul. 1991.

Pelizzari, Charles A., et al., "Accurate Three–Dimensional Registration of CT, PET and/or MR Images of the Brain," *Journal of Computer Assisted Tomography*, 13(1):20–26, Jan./Feb. 1989, pp. 20–26.

Pelizzari, C.A., et al., 3D Patient/Image Registration: Application to Radiation Treatment Planning, *Medical Physics*, vol. 18, No. 3, May/Jun. 1991, p. 612.

Pelizzari, C.A., et al., "Three Dimensional Correlation of PET, CT and MRI Images," *The Journal of Nuclear Medicine, Abstract Book*, 34th Annual Meeting, Toronto, Canada, 1987, vol. 28., No. 4, Poster Session No. 528, p. 682.

Penn, Richard D. et al., "Stereotactic Surgery with Image Processing of Computerized Tomographics Scans," *Neurosurgery*, vol. 3, No. 2, pp. 157–163, Sep./Oct. 1978.

Perry, John H., Ph.D., et al., "Computed Tomography–guided Stereotactic Surgery: Conception and Development of a New Stereotactic Methodology," *Neurosurgery*, vol. 7, No. 4, Oct. 1980, pp. 376–381.

Picard, Claude, et al., "The First Human Stereotaxic Apparatus" *J. Neurosurg.*, vol. 59, pp. 673–676, Oct. 1983.

Piskun, Walter S., Major, et al., "A Simplified Method of CT Assisted Localization and Biopsy of Intracranial Lesions," *Surgical Neurology*, vol. 11, Jun. 1979, pp. 413–417.

Pixsys, Inc., "SACDAC User's Guide, Version 2e" (Mar. 1989) pp. 0–1 through 5–3.

Pixsys, Inc., "Design Aide" (Mar. 1989) 5 unnumbered pages.

Reinhardt, H.F., et al., "CT–Guided 'Real Time' Stereotaxy," Acta Neurochirurgica Suppl. 46, 107–108, 1989.

Reinhardt, H.F., et al., "A Computer Assisted Device for the Intra Operate CT–Correlated Localization of Brain Tumors," (1988) Eur. Surg. Res. 20:52–58.

Reinhardt, H.F., et al., "Mikrochirugische Entfernung tifliegender Gefäßmißbildungen mit Hilfe der Sonar–Stereometrie," Ultraschall in Med. 12 (1991) 80–84.

Reinhardt, H.F., "Surgery of Brain Neoplasms Using 32–P Tumor Marker" Acta Neurochir 97:89–94, (1989).

Reinhardt, H.F., "Sonic Stereometry in Microsurgical Procedures for Deep–Seated Brain Tumors and Vascular Malformations," Neurosurgery, vol. 32, No. 1, Jan. 1993, pp. 51–57.

Reinhardt, H.F., et al., "Interactive Sonar–Operated Device for Stereotactic and Open Surgery," Sterotac Funct Neurosurg, 1990; 54+55:393–397.

Roberts, M.D., David W., et al., "A Frameless Sterotaxic Integration of Computerized Tomographic Imaging and the Operating Microscope," J. Neurosurg., vol. 65, pp. 545–549, Oct. 1986.

Rosenbaum, Arthur E., et al., "Computerized Tomography Guided Stereotaxis: A New Approach," Applied Neurophysiology, vol. 43, No. 3–5, Jun. 4–7, 1980, pp. 172–173.

Sautot, et al., "Computer Assisted Spine Surgery: a First Step Toward Clinical Application in Orthopaedics," IEEE, 1992.

Scarabin, J.M., et al., "Stereotaxic Exploration in 200 Supratentorial Brain Tumors," Neuroradiology, vol. 16, Jun. 4–10, 1978, pp. 591–593.

Shelden, C. Hunter, M.D., et al., "Development of a computerized microstereotaxic method for localization and removal of minute CNS lesions under direct 3–D vision," J. Neurosurg, vol. 52, Jan. 1980, pp. 21–27.

Shiu, Y.C., et al., "Finding the Mounting Position of a Sensor by Solving a Homogeneous Transform Equation of Form AX=XB," IEEE, vol. 3, 1987, pp. 1666–1671.

Smith, Kurt R., et al., "Multimodality Image Analysis and Display Methods for Improved Tumor Localization in Stereotactic Neurosurgery," Annual Conference of the IEEE Engineering in Medicine and Biology Society, vol. 13, No. 1, p. 210, 1991.

Smith, Kurt R., et al., "Computer Methods for Improved Diagnostic Image Display Applied to Stereotactic Neurosurgery," Automedica, vol. 14, pp. 371–382, 1992.

Spencer, et al., "Unilateral Transplantation of Human Fetal Mesencephalic Tissue into the Caudate Nucleus of Patients with Parkinson's Disease" The New England Journal of Medicine, vol. 327, No. 22, pp. 1541–1548, Nov. 26, 1992.

Symon, L. (Hrsg.) et al., Advances and Technical Standards in Neurosrugery, Springer–Verlag, Wien, New York, 1990, pp. 77–118.

Valentino, D.J., et al., Three–Dimensional Visualization of Human Brain Structure–Function Relationships, The Journal of Nuclear Medicine, Oct. 1989, Posterboard 1136, vol. 30, No. 10, p. 1747.

Van Buren, J.M., et al., "A Multipurpose CT–Guided Stereotactic Instrument of Simple Design," Applied Neurophysiology, Jan.–Aug. 1983, pp. 211–216.

Watanabe et al., "Three Dimensional Digitizer (Neuronavigator) : New Equipment for Computed Tomography— Guided Stereotaxic Surgery", 27 Surg. Neurol, 543–47 (1987).

Watanabe, Eiju, M.D., et al., "Neuronavigator," Igaku–no–Ayumi, vol. 137, No. 6, May 10, 1986, pp. 1–4.

Wolfe, William L., "The Infrared Handbook,", Office of Naval Research, Department of the Navy, Washington, D.C., 1978, pp. 22–63 through 22–77.

Wolff, Robert S., et al., "Visualization of Natural Phenomena," The Electric Library of Sciences, 1993, pp. 66–67.

Yeates, Andrew, M.D., et al., "Simplified and accurate CT–guided needle biopsy of central nervous system lesions," Journal of Neurosurgery, vol. 57, No. 3, Sep. 1982, pp. 390–393.

* cited by examiner

SCANNED IMAGE

SURGICAL PROBE
COORDINATE SYSTEM

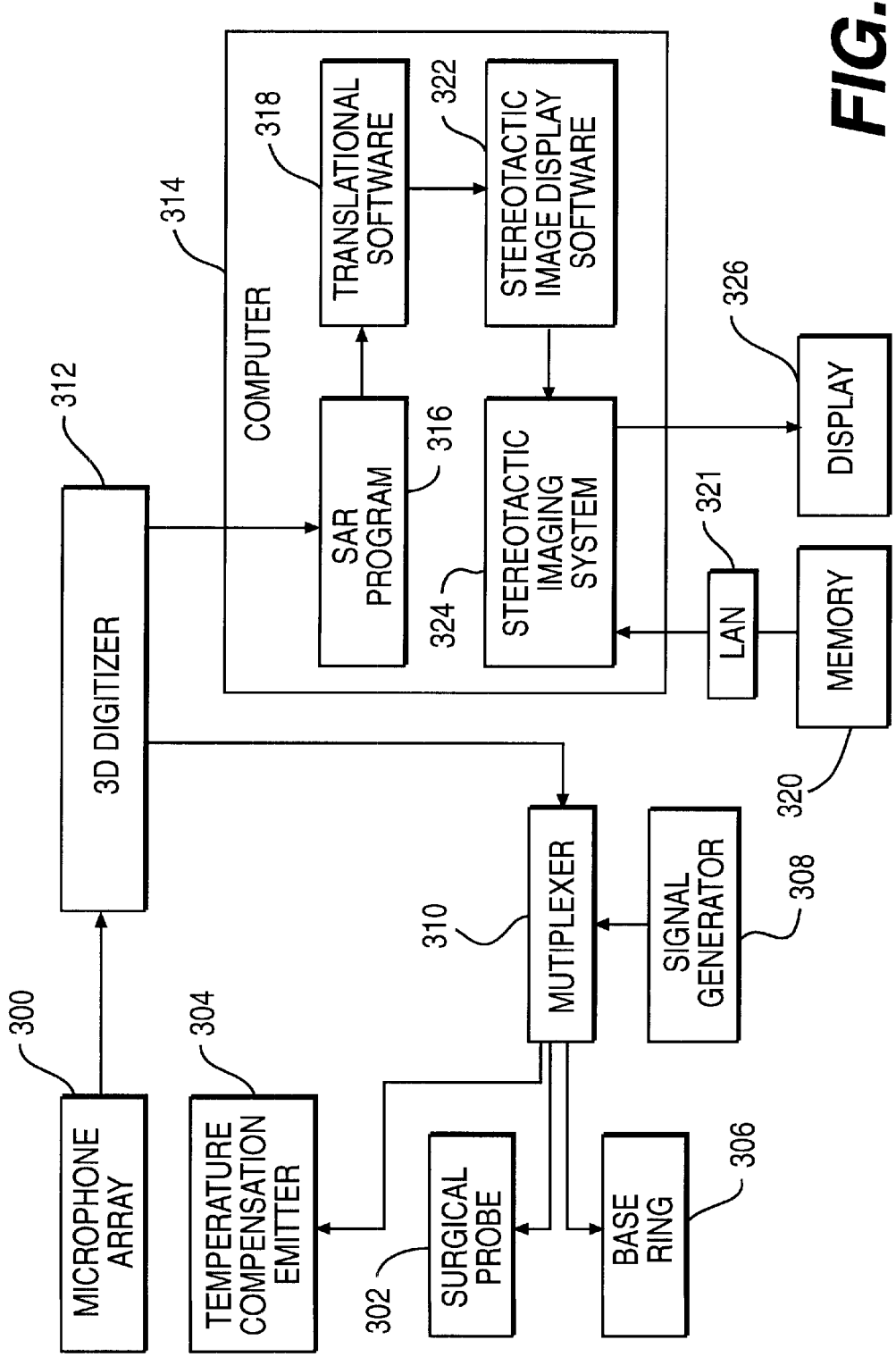

SYSTEM FOR INDICATING THE POSITION OF A SURGICAL PROBE WITHIN A HEAD ON AN IMAGE OF THE HEAD

This application is a continuation of U.S. patent application Ser. No. 09/243,804 filed Feb. 3, 1999, which is a continuation of U.S. patent application Ser. No. 08/477,561 filed Jun. 7, 1995, now U.S. Pat. No. 5,891,034. Application Ser. No. 08/477,561 is a continuation of U.S. patent application Ser. No. 08/053,076 filed Apr. 26, 1993, now abandoned. Application Ser. No. 08/053,076 is a continuation-in-part of U.S. patent application Ser. No. 07/858,980, filed May 15, 1992, now abandoned, which is a national stage application based on PCT/US91/07745, filed Oct. 17, 1991, which PCT is a continuation-in-part of U.S. patent application Ser. No. 07/600,753, filed Oct. 19, 1990, now abandoned. Application Ser. No. 08/053,076 is also a continuation-in-part of U.S. patent application Ser. No. 07/909,097, filed Jul. 2, 1992, now U.S. Pat. No. 5,383,454, which is a continuation of U.S. patent application Ser. No. 07/600,753, filed Oct. 19, 1990, now abandoned—all of which are incorporated herein by reference.

BACKGROUND OF THE INVENTION

Precise localization of position has always been critical to neurosurgery. Knowledge of the anatomy of the brain and specific functions relegated to local areas of the brain are critical in planning any neurosurgical procedure. Recent diagnostic advances such as computerized tomographic (CT) scans, magnetic resonance imaging (MRI) scanning, positron emission tomographic (PET) scanning, and magnetoencephotographic (MEG) scanning have greatly facilitated preoperative diagnosis and surgical planning. However, the precision and accuracy of the scanning technologies have not become fully available to the neurosurgeon in the operating room. Relating specific structures and locations within the brain during surgery to preoperative scanning technologies has previously been cumbersome, if not impossible.

Stereotactic surgery, first developed 100 years ago, consists of the use of a guiding device which channels the surgery through specific parts of the brain as localized by preoperative radiographic techniques. Stereotactic surgery was not widely used prior to the advent of modern scanning technologies as the injection of air into the brain was required to localize the ventricles, fluid containing chambers within the brain. Ventriculography carried a significant complication rate and accuracy in localization was marginal.

SUMMARY OF THE INVENTION

It is an object of this invention to provide a system which can determine the position of a probe within an object and display an image corresponding to the determined position. It is a further object of this invention to provide a system which can determine the position of an ultrasound probe relative to an object and, still further, which can display scan images from other scanning technologies corresponding to the scan images produced by the ultrasound probe. It is a further object of this invention to provide a system which can relate scan images of an object produced with one technology to scan images of the same object produced with another technology.

The invention comprises a system for indicating a position within an object. The system includes reference points means in fixed relation to the object. Means generates images of the object, said images including reference images corresponding to the reference points means. The system also includes reference means located outside the object and a probe including a tip. First means determines the position of the tip of the probe relative to the reference means. Second means measures the position of the reference points means of the object relative to the reference means, so that the position of the tip relative to the reference points means of the object is known. Means translates the determined position of the tip of the probe into a coordinate system corresponding to the images of the object. Means displays an image of the object which corresponds to the translated position of the tip of the probe.

The invention also comprises a system for indicating a position within a body of a patient. The system includes reference points means in fixed relation to the body. Means generates images of the body, said images including reference images corresponding to the reference points means. The system further includes reference means located outside the body and a probe including a tip. First means determines the position of the tip of the probe relative to the reference means. Second means determines the position of the reference points means of the body relative to the reference means, so that the position of the tip relative to the reference points means of the body is known. Means translates the determined position of the tip of the probe into a coordinate system corresponding to the images of as the body. Means displays an image of the body which corresponds to the translated position of the tip of the probe.

The invention also comprises a method for indicating a position of a tip of a probe which is positioned within an object such as a body on images of the body wherein the body and the images of the body include reference images corresponding to a reference point. The method includes the steps of determining the position of the tip of the probe relative to a reference means having a location outside the body; determining the position of the reference points of the body relative to the reference means so that the position of the tip relative to the reference points of the body is known; translating the determined position of the tip of the probe into a coordinate system corresponding to the images of the body; and displaying an image of the body which corresponds to the translated position of the tip of the probe.

The invention also comprises a system for determining a position of an ultrasound probe relative to a part of a body of a patient wherein the probe is positioned adjacent to and scanning the body part. An array is positioned in communication with the probe. First means determines the position of the ultrasound probe relative to the array. Second means determines the position of the body part relative to the array. Means translates the position of the ultrasound probe into a coordinate system corresponding to the position of the body part.

The invention also comprises a system for relating scan images of a body of a patient. The scan images are produced from first and second scanning technologies. The system includes reference points means in fixed relation to the body. Means relates the first scanned images to the reference points means. Means relates the second scanned images to the reference points means. Means selects a particular first scanned image. Means determines the position of the particular first scanned image relative to the reference points means. Means generates a second scanned image which has the same position relative to the reference points means as the determined position so that the generated second scanned image corresponds to the particular first scanned image.

The invention also comprises apparatus for indicating a position relative to a body of a patient. The apparatus comprises radiopaque markers and means for noninvasively supporting the markers on the surface of the skin of the body. The supporting means may comprise a sheet of material overlying the body, and means on the sheet of material for supporting the markers.

The invention may be used with a scanner for scanning a body part of a patient in order to generate images representative of the body part. The improvement comprises means for marking the surface of the skin on the body part with a radiopaque material, whereby the generated images include images of the marking means.

Other objects and features will be in part apparent and in part pointed out hereinafter.

BRIEF DESCRIPTION OF THE DRAWINGS

FIG. 3A is a block diagram of one system of the invention for indicating the position of a surgical probe within a head on an image of the head.

Corresponding reference characters indicate corresponding parts throughout the several views of the drawings.

DETAILED DESCRIPTION OF THE PREFERRED EMBODIMENTS

With the advent of modern scanning equipment and techniques, several stereotactic systems have been developed and are presently available. These stereotactic systems allow a surgeon to localize specific points detected on CT, MRI, PET, or MEG scans which have been previously generated prior to the surgical procedure being performed. In particular, the stereotactic systems allow the selection of specific points detected on the scans to be localized within the brain by the surgeon during the surgical procedure using a mechanical device.

Figure 1A:
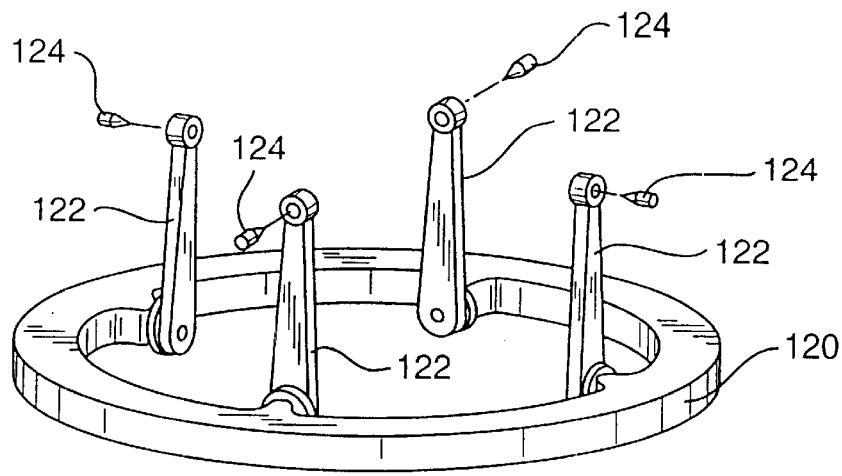
FIG. 1A is a perspective illustration of a reference ring of the prior art which is mounted by uprights to a patient's head to support the cylindrical frame structure of FIG. 1B or the ring 306 of FIG. 3B.

In use, the prior art stereotactic systems often require a base such as a ring 120 (also known as a BRW head ring) in FIG. 1A. Ring 120 is firmly attached to the patient's skull via uprights 122 and sharp pins 124 throughout scanning and surgery.

Figure 1B:
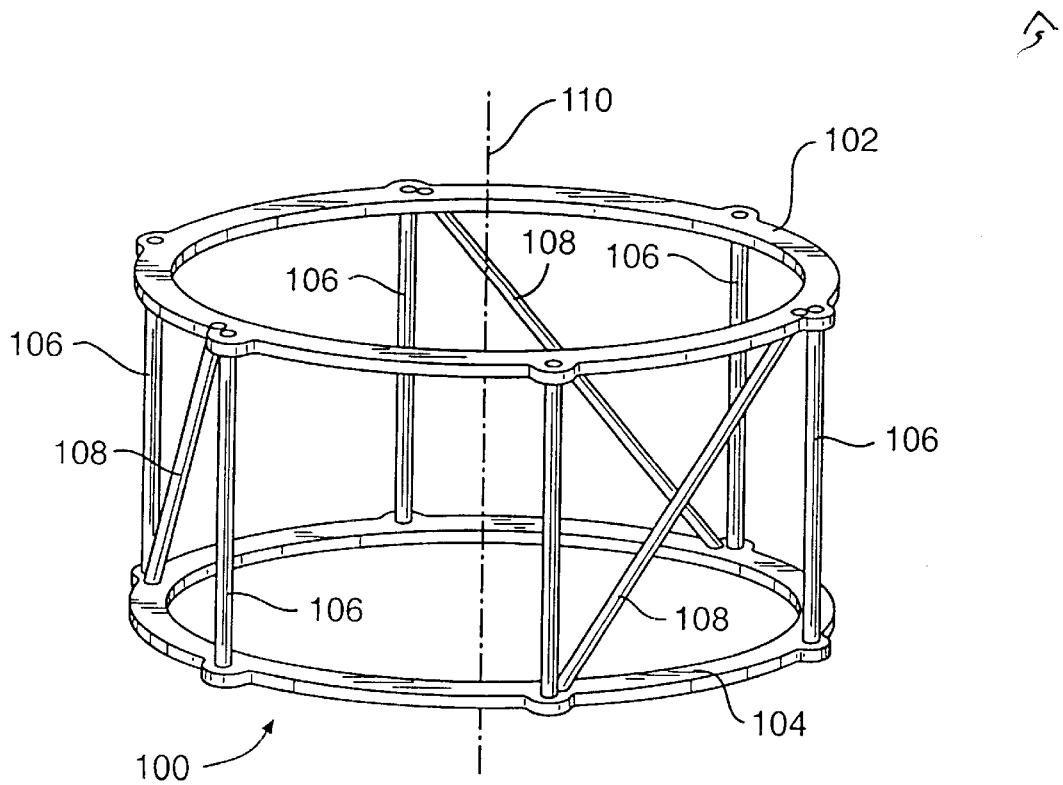
FIG. 1B is a perspective illustration of a cylindrical frame structure of the prior art which is mounted around a patient's head during the scanning process.
Figure 1C:
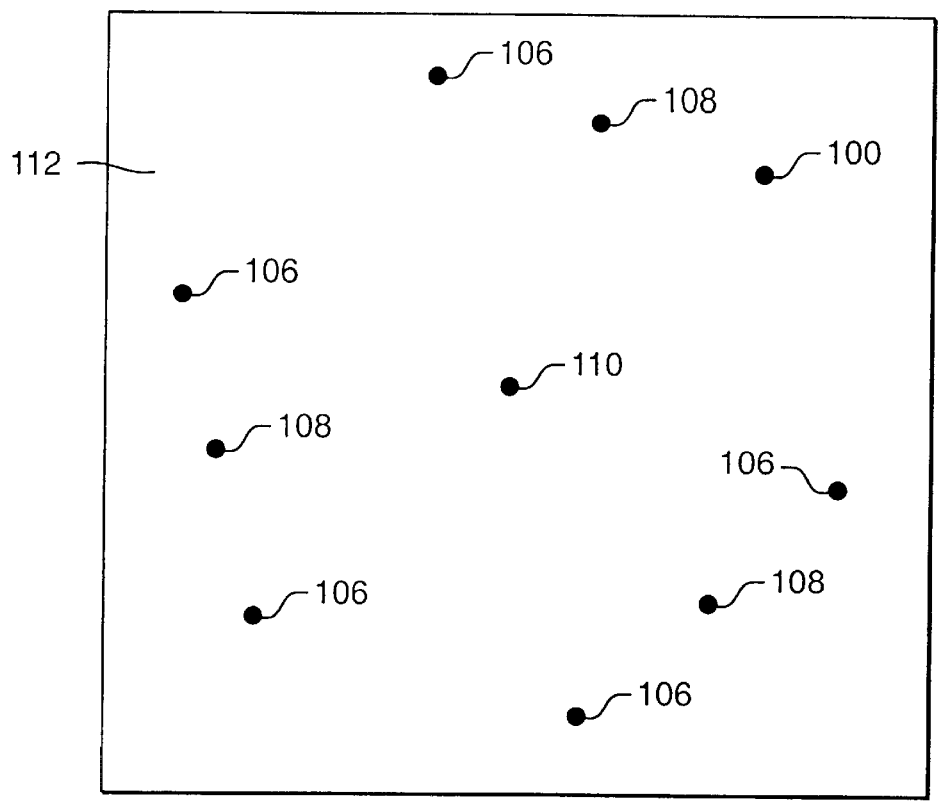
FIG. 1C is a plan view according to the prior art of the rods of the cylindrical frame structure of FIG. 1B taken along a plane midway between the upper and lower rings.

During scanning, some form of localizing device, such as a cylindrical structure 100 in FIG. 1B, is attached to ring 120. Structure 100 comprises an upper circular ring 102 in parallel with a lower circular ring 104. Lower ring 104 is mounted to reference ring 120 so that the three rings 102, 104 and 120 are in parallel planes. Rings 102 and 104 are interconnected by six vertical rods 106 and three diagonal rods 108. These specific marking rods are also called fudicels. The three diagonal rods 108 diagonally interconnect rings 102 and 104. Any plane orthogonal to an axis 110 of structure 100 which passes through structure 100 will create a unique pattern of six cross sectional views of rods 106 and three cross sectional views of rods 108. The resultant spacing between the diagonal and upright rods defines a unique orthogonal plane within structure 100. FIG. 1C shows, for example, the spacing of the rods when the position of the scan plane 112 is parallel to and midway between rings 102 and 104 of structure 100.

Figure 1D:
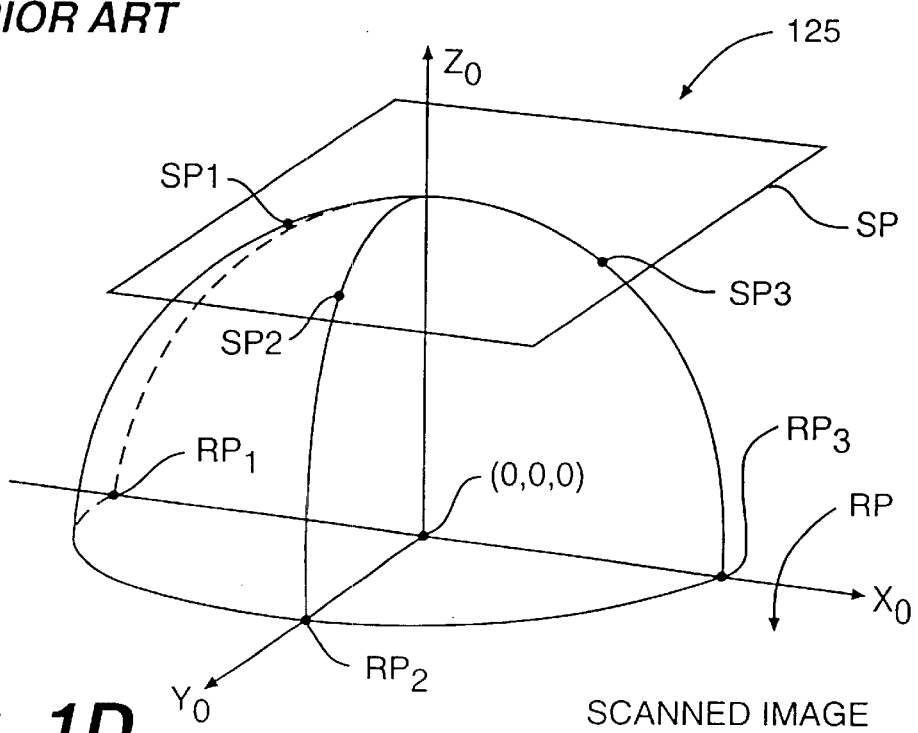
FIG. 1D is a perspective illustration of the coordinate system of a three dimensional scanned image.

After the scanning process, the images obtained are analyzed and the position of rods 106 and 108 shown in the images is measured. By knowing the position of rods 106 and 108, the specific location of a scan with respect to structure 100 and therefore with respect to base ring 120 can be determined. As shown in FIG. 1D, the scans can be arranged within a scanned image coordinate system 125 with the reference plane RP set in fixed relation to the position of ring 120. A scan plane SP can be defined within the scanned image coordinate system 125 by at least three reference points SP1, SP2 and SP3 located on the head of the patient. By associating a scan image with a scan plane SP in the scanned image coordinate system, a point on the scan can be identified with a point in the patient's head.

Figure 2A:
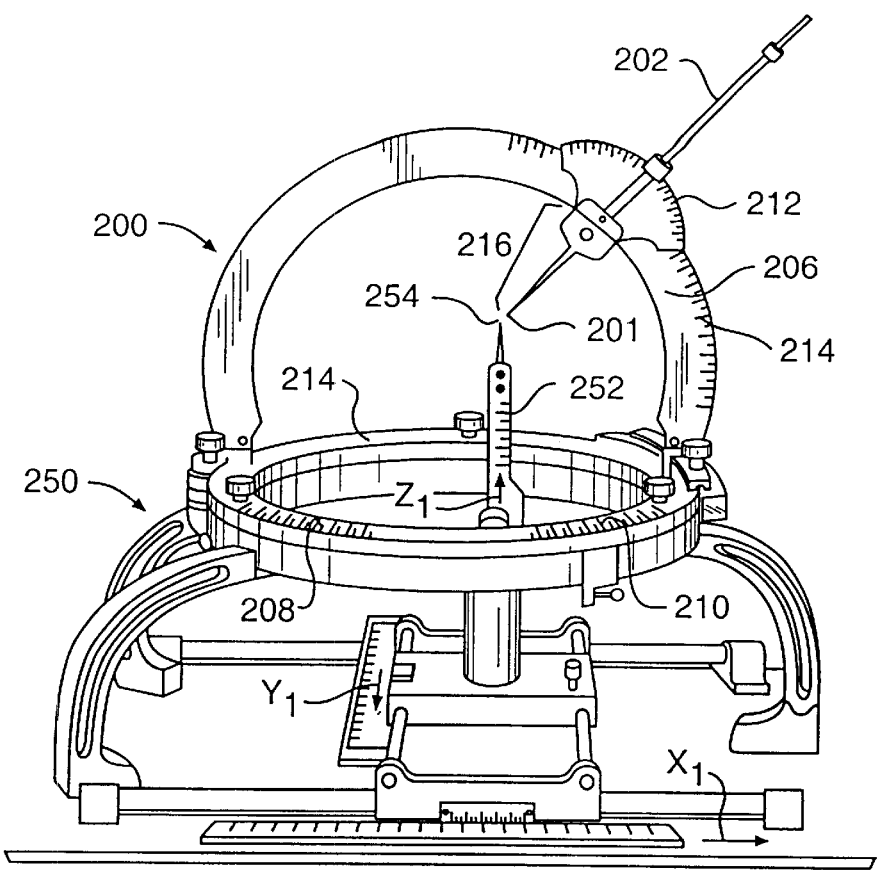
FIG. 2A is a perspective view of the caliper frame of the prior art used to target a position in the brain and to determine a position in the head relative to the phantom base.
Figure 2B:
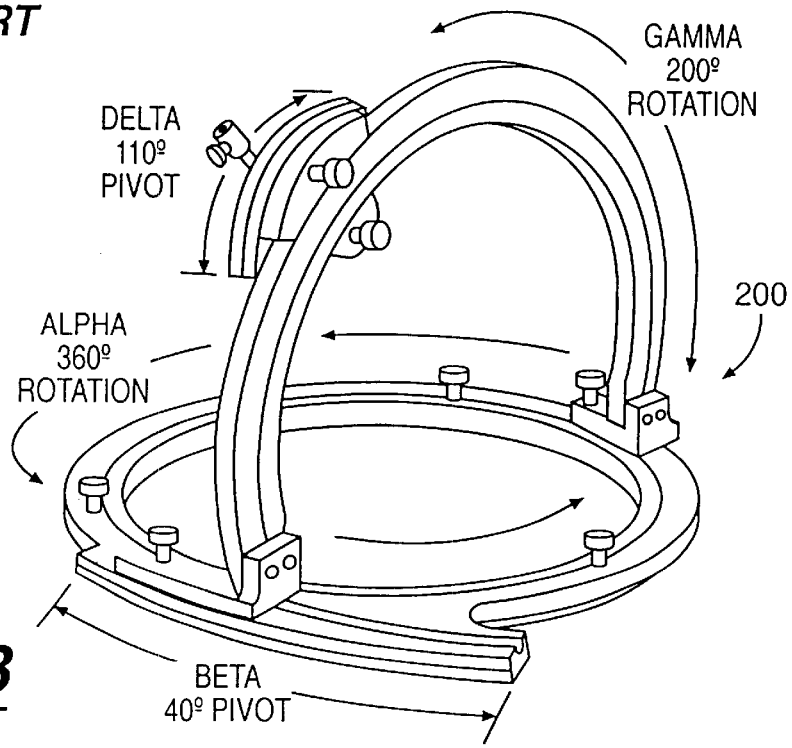
FIG. 2B is a perspective view of the caliper frame of the prior art of FIG. 2A illustrating its angles of adjustment.

During surgery, the surgeon can use the stereotactic system to calculate a specific position within the brain corresponding to a scan image and then target that portion of the brain with a probe. First, the structure 100 used during scanning is removed from ring 120 and a specially designed caliper frame 200, as illustrated in FIG. 2A, is attached to ring 120. Frame 200 holds a surgical probe 202 which is positioned on an arch 206 for insertion into the patient's head. Frame 200 indicates the alpha, beta, gamma and delta angles on scales 208, 210, 212 and 214 for directing probe 202 to a particular target, as shown in FIG. 2B. The distance 216 from the tip of probe 202 to arch 206 is also determined. A computer is then used to correlate the position of the targeted scan image in the scanned image coordinate system with the corresponding angles alpha, beta, gamma and delta and distance 216 on frame 200 to enable the surgeon to apply the probe to the targeted area of the brain. A target picked out on a scan of a specific image can be approached with a fair degree of accuracy using this surgical procedure.

Figure 2C:
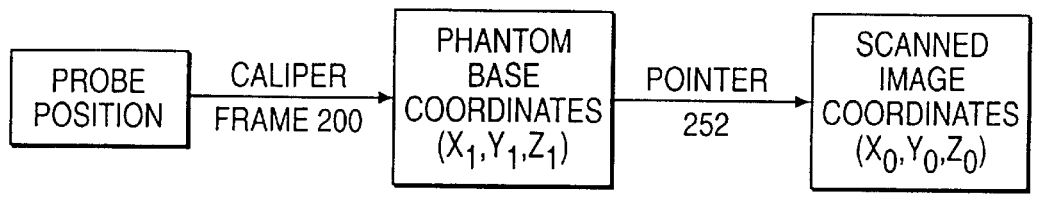
FIG. 2C is a block diagram of the steps involved in the prior art process of determining the position of a probe relative to the scanned images so that the image corresponding to the probe position can be identified and viewed by the surgeon.

In the past, the surgeon has also used the stereotactic system in reverse in order to determine the position of the probe 202 in the brain relative to the scanned images so that the scan image corresponding to the probe position can be identified and viewed. To do this, the surgeon again attaches frame 200 to ring 120. Probe 202 is then positioned in frame 200 and inserted into the brain. Frame 200 is then removed from ring 120 and mounted to a phantom base 250 in a manner as illustrated in FIG. 2A. Phantom base 250 has a coordinate system $(X_1, Y_1, X_1)$. Generally, caliper frame 200 identifies a point 201 over phantom base 250. A pointing device 252 is positioned to have its tip 254 at point 201. The $X_1-Y_1$ plane of phantom base 250 is parallel to the plane in which the reference points RP1, RP2 and RP3 are located. The $(X_1, Y_1, Z_1)$ coordinates define the position of point 201. As a result, the position of point 254 with respect to the $X_1-Y_1$ plane and, therefore, with respect to the reference plane RP is now known. A computer is used to calculate the specific position within the brain and the particular scan which corresponds to the calculated position can now be accessed and viewed on a scanning system. This prior art process is shown in diagram form in FIG. 2C.

After this cumbersome and time-consuming process, the surgeon has now determined the position of the tip 201 of probe 202 with respect to the scanned images and can now view the image corresponding to the probe position to decide the next step in the surgical procedure. This entire process takes approximately ten to fifteen minutes and increases the risks of intraoperative contamination as the base of frame 200 is nonsterile. Because of these considerations, this surgical procedure is not commonly performed.

Although stereotactic surgery as performed with the apparatus of the prior art allows a surgeon to be guided to a specific point with accuracy, it has not been particularly useful in allowing the surgeon to identify the particular location of a probe within the brain at any point during the surgical process. Frequently in neurosurgery, brain tumors or other target points within the brain are indistinguishable from surrounding normal tissue and may not be detected even with the use of frozen sections. Moreover, with modern microsurgical techniques, it is essential that the neurosurgeon identify specific structures within the brain which are of critical functional importance to the patient. The boundaries of these structures must be accurately defined and specifically known to the surgeon during the surgical process. In this way, these tissues will not be disturbed or otherwise damaged during the surgical process which would otherwise result in injury to the patient. The minimal accuracy afforded by stereotactic surgery is generally insufficient for modern microsurgical techniques. Consequently, stereotactic surgery is not generally available to the majority of patients undergoing surgery.

The present invention solves these problems by allowing the surgeon to retrieve and display quickly the scanned image which corresponds to the current position of a tip 301 of a surgical probe 302. A cursor appears on the displayed scan to show the position of probe tip 301 within the displayed scan. FIGS. 3A–3C and 5 illustrate a system of the invention which includes sound emitters 360 and 370 and microphone detectors 350 and associated hardware to determine the position of probe tip 301 relative to a reference ring 306 on the patient's head. Because the position of the scanned images relative to reference ring 306 is known from the scanning procedure, the position of probe tip 301 relative to the scanned images is known and the relevant image can be displayed. FIGS. 3A and 4A–8 illustrate a system of the invention which includes infrared emitters 540 and 545 and detectors 550 in place of the sound emitters 360, 370 and microphone detector 350 for determining the position of a reference bar 548 and a probe tip 541. A computer 396 and an infrared scanner 380 relate the scanned images to the shape of the forehead and relate the shape of the forehead to the position of reference bar 548. Reference bar 548 is then associated with the scanned images through the forehead shape without the use of the cylindrical reference frame 100 during scanning. The use of the forehead shape as a reference point also allows the scanned images from different scanning technologies to be interrelated. As an alternative to reference ring 306 and reference bar 548 described above, FIG. 3D uses reference pins 307 affixed to the skull for determining the position of the patient's head during surgery. As a further alternative, FIGS. 9–11 use a removable cap for holding markers during scanning. The positions of the markers are marked on the head for later use during surgery in registering the surgical space with the scan images. FIG. 6 includes an ultrasound probe 500 for use during surgery. Other advantages are also provided as more fully described below.

Figure 2D:
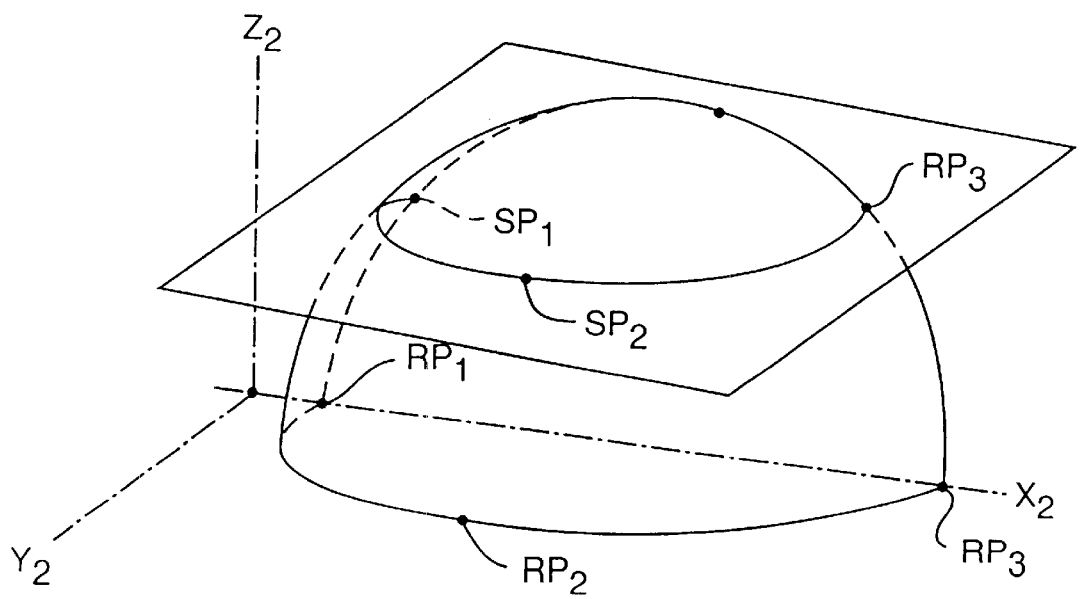
FIG. 2D is a perspective illustration of a three dimensional coordinate system of a probe.

In relating the position of a probe tip e.g., probe tip 301, to a scanned image, it can be seen in FIGS. 1D and 2D that the surgeon must know the specific location of tip 301 with respect to the scanned image coordinate system $(X_0, Y_0, Z_0)$ of the scans that were preoperatively performed. In other words, probe tip 301 has a particular coordinate system $(X_2, Y_2, Z_2)$ which is illustrated in FIG. 2D. Ideally, the surgical probe coordinate system $(X_2, Y_2, Z_2)$ must be related to the scanned image coordinate system $(X_0, Y_0, Z_0)$. The prior art as illustrated in FIG. 2B has suggested relating these coordinate systems via the phantom base coordinate system $(X_1, Y_1, Z_1)$. However, as noted above, this relational process is inaccurate, time-consuming and cumbersome. The invention uses a 3D digitizer system to locate the position of probe tip 301 within the probe coordinate system $(X_2, Y_2, Z_2)$ and to relate it to the scanned image coordinate system $(X_0, Y_0, Z_0)$.

Figure 3B:
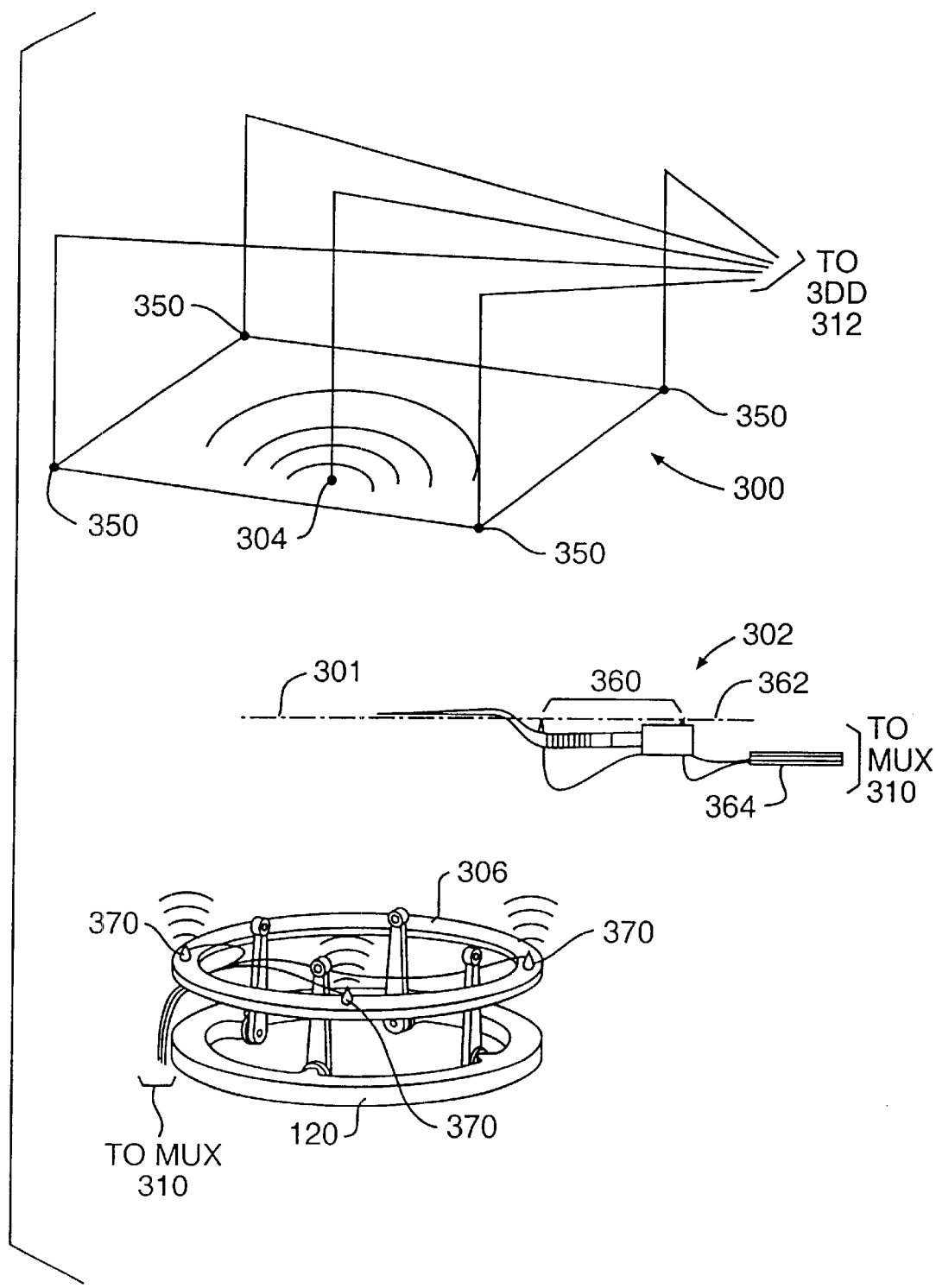
FIG. 3B is a perspective schematic diagram of a microphone array, probe and base ring according to one system of the invention.

FIGS. 3A and 3B show a microphone array 300, a temperature compensation emitter 304, a surgical probe 302, and a base ring 306. Microphone array 300 includes a plurality of microphones 350 which are preferably spaced one meter apart. Microphones 350 may be attached to the operating light above the patient's head in direct line of sight of all of the emitters 360 and 370. Microphones 350 thereby detect the sound emitted from the emitters. Surgical probe 302 preferably is a surgical coagulating forceps such as a bipolar coagulating forceps. Probe 302 could also be a drill, suction tube, bayonet cauterizing device, or any other surgical instrument modified to carry at least two sound emitters 360 thereon for determining position. Emitters 360 on probe 302 are essentially coaxial on an axis 362 with tip 301. Emitters 360 are in line and immediately below the surgeon's line of sight so that the line of sight is not blocked. Probe 302 has a bundle of wire 364 attached thereto for connection to an electrical power source. The wires required to energize emitters 360 are combined with bundle 364. The surgeon is familiar with handling such a probe connected to a wire bundle; therefore, this apparatus does not inconvenience the surgeon. During surgery, ring 306 is affixed to the reference ring 120 attached to the patient's head and is essentially coplanar with it. Ring 306 includes a plurality of emitters 370 which are preferably positioned 90 degrees apart with the center emitter being located at the anterior of the head. This permits ring 306 to be mounted around the head so that all three emitters are in line of sight with array 300.

In use, the position of each of emitters 360 and 370 is determined individually in order to determine the position of the devices to which the emitters are attached. This is accomplished by rapidly energizing the emitters one at a time in a predetermined sequence and measuring the time required for the individual sounds to reach each of microphones 350 in array 300. A 3D digitizer 312 controls this operation through a signal generator 308 and a multiplexer 110. Digitizer 312 may be an off-the-shelf Model GP-8-3D three dimensional sonic digitizer produced by Scientific Accessories Corporation. Under the control of digitizer 312, multiplexer 310 applies an energizing signal from signal generator 308 first to a temperature compensation emitter 304, then sequentially to emitters 370 on ring 306, then sequentially to emitters 360 on probe 302. During this time, digitizer 312 receives and digitizes the output signals produced by microphones 350 in response to the energizations of the emitters. The digitized output signals are output to a computer 314.

Computer 314, following the flow chart shown in FIG. 5 as more fully described below, is programmed with the predetermined pattern and timing for energizing emitters 360 and 370. Computer 314 includes a spatial acquisition and recording (SAR) program 316 which acquires and records spatial coordinates based on the digitized signals. For example, the SAR program 316 may be the SACDAC program licensed by PIXSYS of Boulder, Colo. SAR program 316 measures the time of transmission from each of the emitters to each of the microphones 350. By comparing these times, SAR program 316 calculates the position of each of emitters 360 and 370. Since ring 306 contains three emitters 370, SAR program 316 can calculate the position of ring 306 through standard geometric computations. This plane essentially defines the reference plane of the scan images because it is coplanar with the reference points RP1, RP2 and RP3 in the scanning coordinate system of FIG. 1D. Similarly, since probe 302 contains two emitters 360, SAR program 316 can calculate the position of probe tip 301 through standard geometric computations. After SAR program 316 determines the respective positions of ring 306 and probe tip 301 relative to array 300, it next determines the position of ring 306 relative to tip 301 within the probe coordinate system of FIG. 2D.

One consideration in using sound emitters to determine position is that the speed of the emitted sound will vary with changes in the temperature of the air in the operating room. In other words, since the system is very accurate, the period of time that it takes from the instant a particular emitter 360 or 370 is energized to emit sound until the instant that each of microphones 350 of array 300 receives the sound will vary with air temperature. In order to calibrate the system for these changes, temperature compensation emitter 304 is located in a fixed position relative to array 300. Temperature compensation emitter 304 may be, for example, a sonic digitizer as is used in the Scientific Accessories Corporation Model GP-8-3D. SAR program 316 knows, through calibration, the distance between temperature compensation emitter 304 and each of the microphones 350 of array 300. The speed of sound transmitted from temperature compensation emitter 304 to microphones 350 is measured by the SAR program and compared against the known distance to determine the speed at which the sound is being transmitted through the air. Therefore, SAR program 316 can immediately calculate the reference standard, i.e., the velocity of the emitted sound through the air. This instantaneous reference is applied to the sound emitted from the other emitters 360 and 370 to determine accurately the position of the other emitters.

After SAR program 316 has accurately determined the position of probe tip 301 in the probe coordinate system shown in FIG. 2D, it outputs the coordinates to translational software 318 in computer 314. Translational software 318 then translates the coordinates from the surgical probe coordinate system of FIG. 2D into the scanned image coordinate system shown in FIG. 1D, as more fully described below. A memory 320 accessed through a local area network (LAN) 321 stores each of the images of the preoperative scan according to the respective positions of the scans within the scanned image coordinate system of FIG. 1D. The respective positions of the scans are known from the position of rods 106 and 108 in the scans, which information is stored in memory 320. The translated coordinates generated by translational software 318 are provided to stereotactic image display software 322, also resident within computer 314. Stereotactic image display software 322 actuates a stereotactic imaging system 324 to generate a scan image from the data stored in memory 320 corresponding to the translated coordinates. Stereotactic imaging system 324 displays the generated image on a high resolution display 326. Display 326 preferably displays the axial, saginal and coronal views corresponding to probe tip 301. Stereotactic image display software 322 and stereotactic image system 324 may be any off-the-shelf system such as manufactured by Stereotactic Image Systems, Inc. of Salt Lake City, Utah. This cycle of calibrating the system through temperature compensation emitter 304, sequentially energizing emitters 370 and 360 to determine the respective positions of ring 306 and probe 302, and generating and displaying a scan image corresponding to the position of probe tip 301 all occur each time the surgeon closes a switch to activate the system. The switch (not shown) may be positioned on probe 302, in a floor pedal (not shown), or wherever else may be convenient to the surgeon.

As seen above, ring 306 is one apparatus for determining and positioning the reference points RP1, RP2 and RP3 with respect to microphone array 300. An advantage of ring 306 is that, each time emitters 360 on probe 302 are energized, emitters 370 on ring 306 are also energized to redefine the reference plane. This allows the surgeon to move the patient's head during surgery.

Figure 3C:
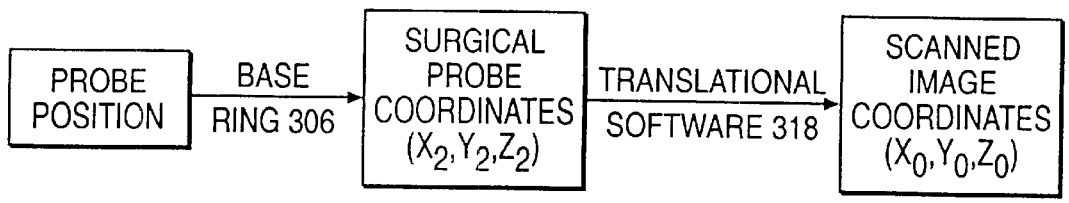
FIG. 3C is a block diagram of the steps involved in the process according to the invention for determining the position of a surgical probe relative to the scanned images so that the image corresponding to the probe position can be identified and viewed by the surgeon.
Figure 3D:
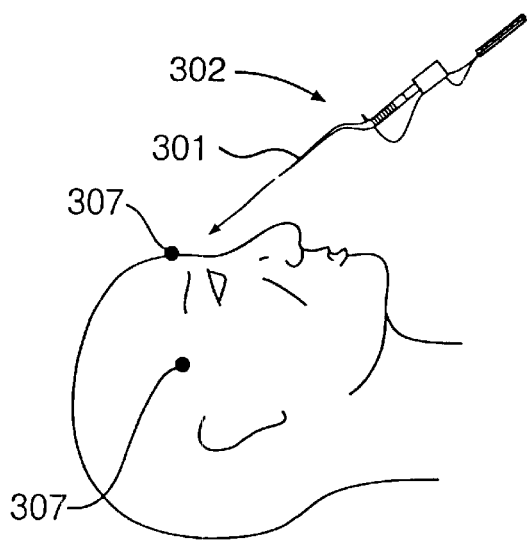
FIG. 3D is an illustration showing three reference points on a head for use as a frame of reference during preoperative scanning and surgery.

Alternatively, as shown in FIG. 3D, the reference points RP1, RP2 and RP3 can be established with the 3D digitizer 312 and three reference pins 307. Reference pins 307 are radiolucent surgical screws with radiopaque tips. Pins 307 are permanently affixed to the patient's skull before surgery and before the preoperative scanning. The radiopaque tips thereby provide a constant reference during scanning and throughout the stereotactic surgical procedure. During surgery, probe tip 301 is positioned on each of pins 307 and actuated to emit a signal which is detected by microphone array 300 and output to 3D digitizer 312. This allows the position of tip 301 to be determined at each of these points. This is performed during a reference mode of operation of 3D digitizer 312. At the end of the reference mode, SAR program 316 calculates the position of the reference points RP1, RP2 and RP3. The use of pins 307 requires that the reference points have to be reestablished before the position of probe 302 is determined to avoid changes in the reference plane due to movement of the head. A further variation contemplates that emitters 370 may each be separately mounted to pins 307 or other fixed structures positioned at each of the reference points.

In summary, this process according to the invention is illustrated in FIG. 3C and identifies the location of probe tip 301 for the surgeon. Initially, the reference plane is determined by energizing ring 306 or by positioning probe tip 301 at the reference points. Next, the emitters of probe 302 are energized so that the position of probe tip 301 in the head is determined in the probe coordinate system ($X_2$, $Y_2$, $Z_2$). Translational software 318 then converts the probe coordinate system into the scanned image coordinate system ($X_0$, $Y_0$, $Z_0$) so that the image corresponding to the position of probe tip 301 can be generated and displayed.

Figure 4A:
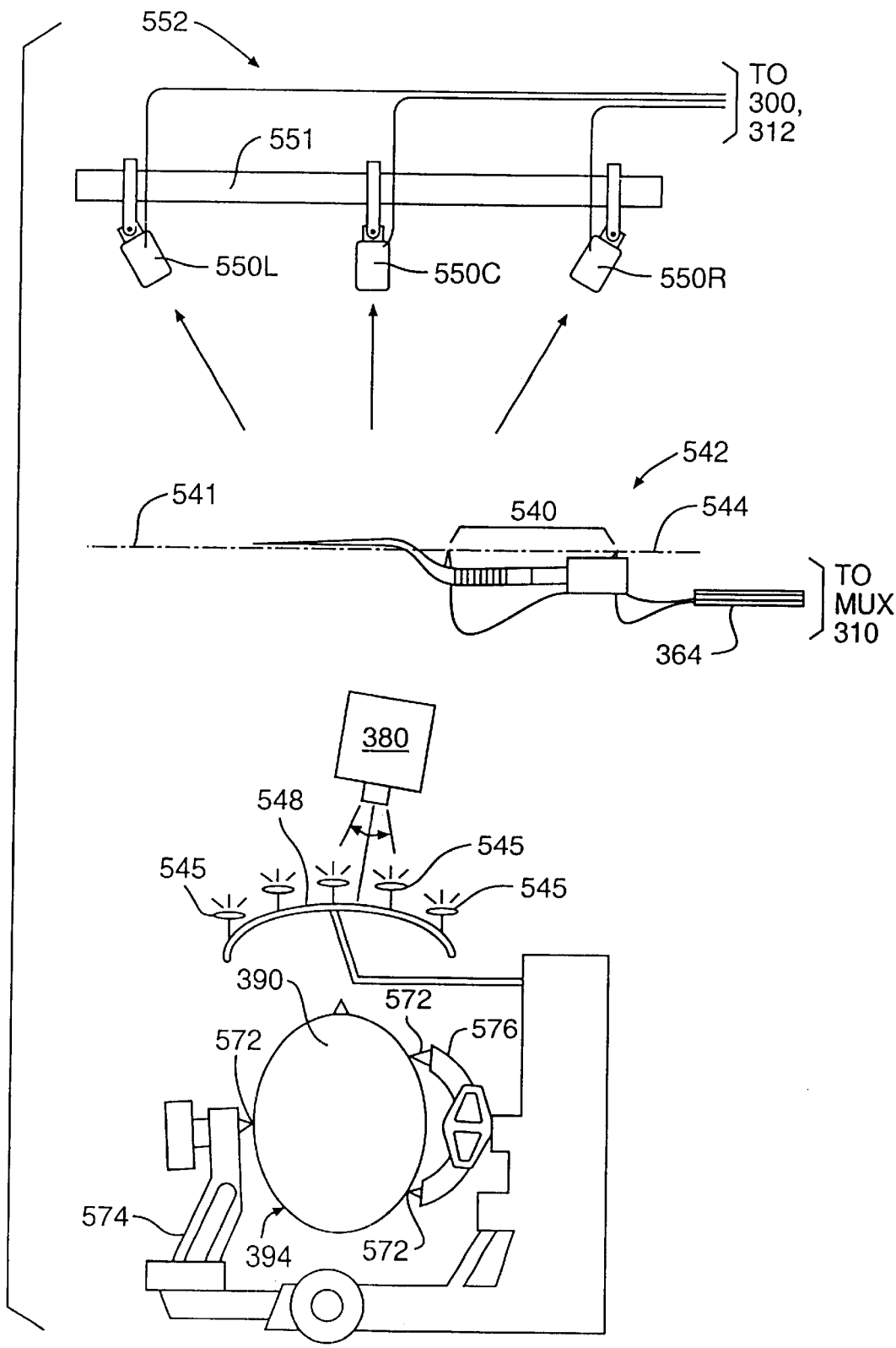
FIG. 4A is a perspective schematic diagram of an infrared detector array, probe, reference bar, clamp and optical scanner according to one system of the invention.

In another system of the invention as shown in FIG. 4A, infrared emitters 540 and 545 and an array 552 of detectors 550 are used respectively in place of sound emitters 360 and 370 and microphones 350 of FIG. 3B. Fixed reference bar 548, a surgical probe 542, and related components are used in place of ring 306, probe 302, and related components of FIG. 3B. A Mayfield clamp 570 of known construction is used in place of ring 120 for rigid attachment to the patient's head 394. Clamp 570 includes sharp pins 572 attached to adjustable jaws 574 and 576. Clamp 570 is thereby adjusted for rigid attachment to head 394. Reference bar 548 is rigidly attached to clamp 570 so that there is no relative movement between bar 548 and head 394. No temperature compensating emitter such as emitter 304 in FIG. 3B is required in FIG. 4A because the apparatus of FIG. 4A uses the position of emitters 540 and 545 as viewed by detectors 550 (as more fully explained below) to determine probe and ring positions instead of the time of transmission of the emitted signal as with the embodiment of FIG. 3B.

In use, infrared detectors 550 are attached to a mounting bar 551 in fixed relation to each other. Detectors 550 are generally positioned so that their views converge on a phantom point. For example, the two outer detectors 550L and 550R may view a field of two intersecting vertical planes and the center detector 550C would view a horizontal plane. This can be accomplished by employing vertical slits on the field of view of the outer detectors and a horizontal slit on the field of view of the center detector. The phantom point is set to be in the general vicinity of the patient's forehead 390. Mounting bar 551 is suspended from the operating room light in direct line of sight of the patient's forehead 390 and of emitters 540 and 545. Detectors 550 thereby detect the infrared light emitted from emitters 540 and 545. Detectors 550 include a large number of linear chip cameras such as CCD (charge coupled device) cameras or pixels. A cylindrical lens (not shown) may also be used behind the slits in detectors 550 to collimate the infrared light. By knowing which particular pixel of the large number of pixels found in each of the three detectors 550 receives the infrared light from emitters 540 and 545, the angle to a particular emitter from each of detectors 550 can be determined and, therefore, the positions of each of emitters 540 and 545 can be determined using conventional mathematical analysis. Accordingly, the position of probe tip 541 within the scan image coordinate system is known.

Figure 4B:
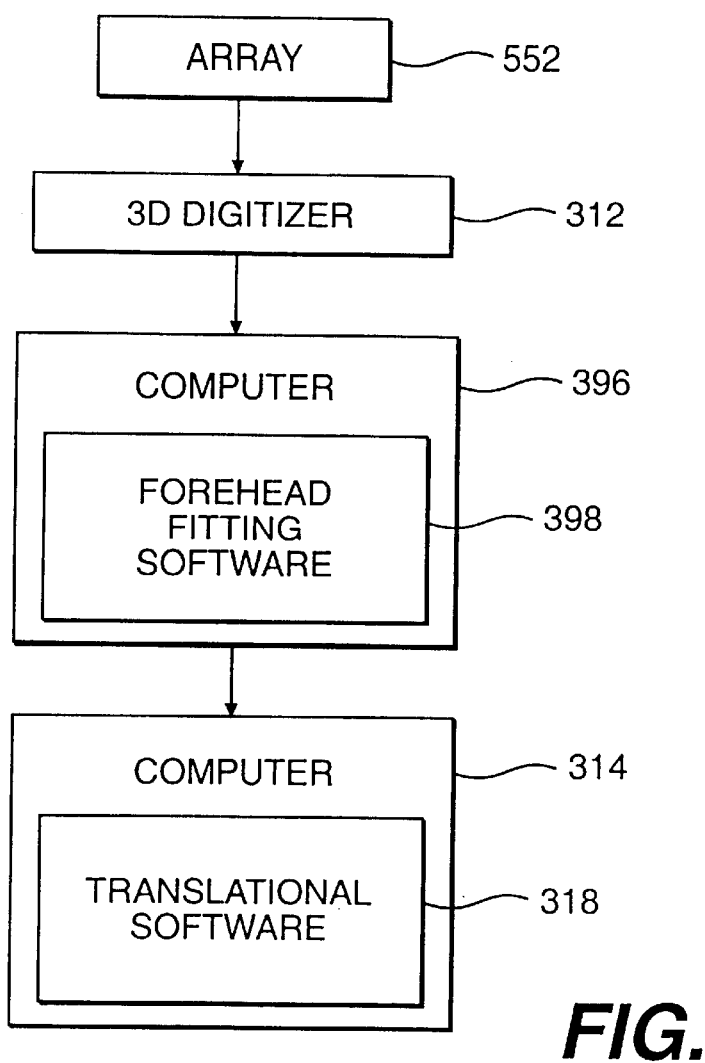
FIG. 4B is a block diagram of a system for use with the apparatus of FIG. 4A for determining the contour of a forehead.
Figure 5:
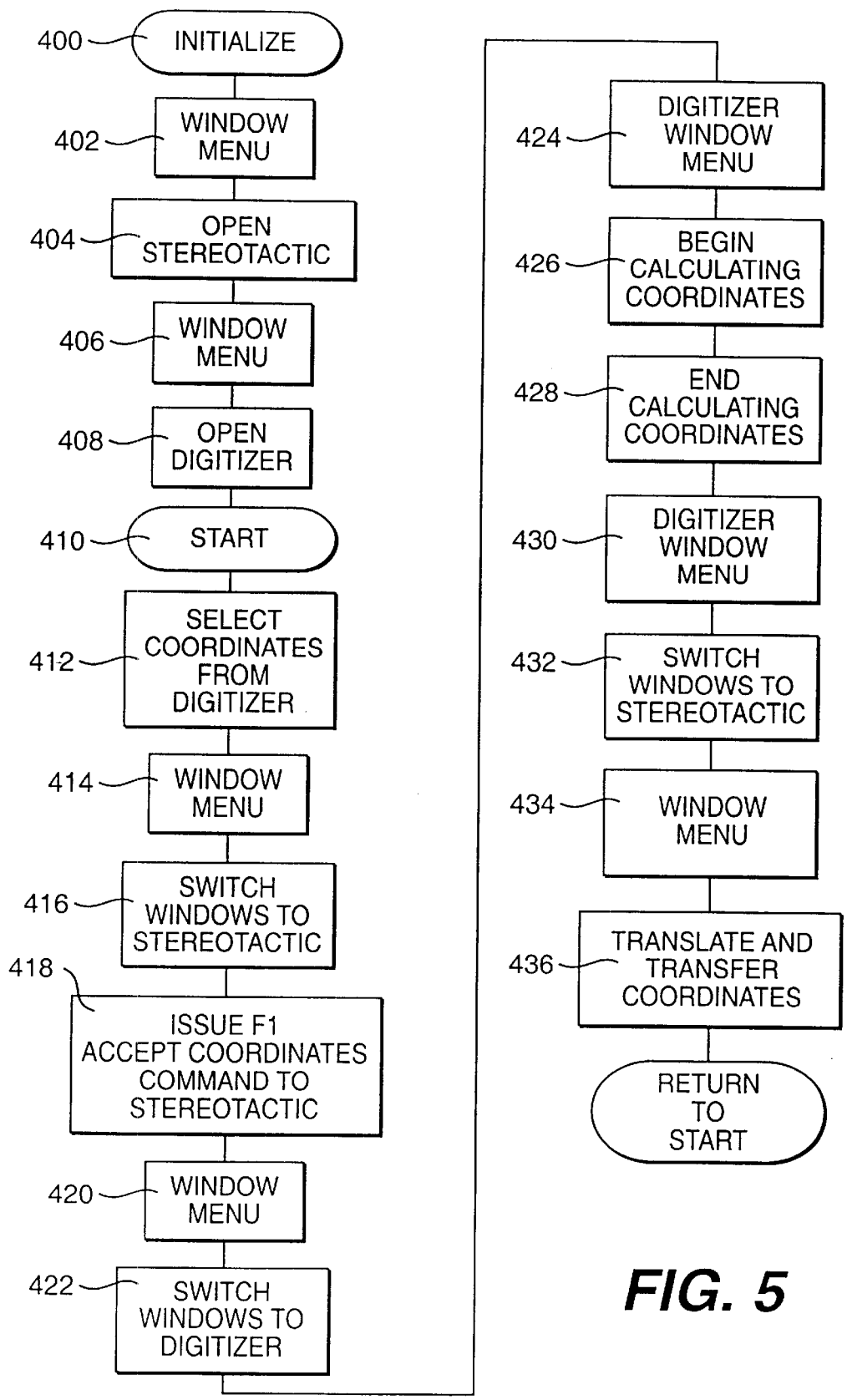
FIG. 5 is a flow chart of the translational software for translating coordinates from the probe coordinate system to the scanned image coordinate system according to the invention.

The apparatus of FIGS. 4A, 4B, 6A, 7 and 8 may be controlled with the computer and other hardware shown in FIG. 3A using the software shown in FIG. 5. Apart from the use of infrared light in place of sound and the measurement of the position of the emitters through geometry instead of the timed delay of sound, the operation of this hardware and software parallels the operation disclosed above.

An advantage of using infrared light is that it allows for the use of the contour of a portion of the patient's head 394, preferably the forehead 390 above and around the patient's eyes, to relate the position of the probe 542 to the scan images. This is accomplished with an optical scanner 380 which generates an infrared laser beam which is reflected off of the patient's forehead 390 in timed sequence with the firing of emitters 545 to determine the forehead contour relative to reference bar 548. Such optical scanning of the forehead allows preoperative scanning to occur well in advance of anticipated surgery and without intubation. Other benefits and features of the improvement are more fully explained below.

In particular, FIGS. 4A and 4B include infrared detector array 552, probe 542, reference bar 548 and optical scanner 380. Surgical probe 542 preferably is a surgical coagulating forceps such as a bipolar coagulating forceps. Probe 542 could also be a drill, suction tube, bayonet cauterizing device, or any other surgical instrument modified to carry at least two infrared emitters 540 thereon for determining position. Emitters 540 on probe 542 are essentially coaxial on an axis 544 with tip 541. Emitters 540 are in line and immediately below the surgeon's line of sight so that the line of sight is not blocked. Probe 542 has a bundle of wire 364 attached thereto for connection to an electrical power source. The wires required to energize emitters 540 are combined with bundle 364. Bar 548 comprises a bar with a plurality of at least three infrared emitters 545 positioned thereon. During surgery, the line of sight between some of the emitters 545 and the array 552 may be blocked by a surgical hose or other object. This could temporarily prevent array 552 from detecting the position of bar 548. Accordingly, it is preferable to place more than three emitters (e.g., seven or eight emitters) on bar 548 so that the line of sight for at least three emitters is always maintained. Such additional emitters can also be used to more precisely locate the position of bar 548. Bar 548 which holds emitters 545 is also preferably positioned slightly away from head 394 for increased clearance around head 394 and to reduce the number of instances where the line of sight between emitters 545 and array 552 is blocked. Optical scanner 380 is generally located in front of the patient's forehead 390. Optical scanner 380 and its associated software to generate a forehead image are standard, off-the-shelf components such as those used to scan an object to determine its three-dimensional shape. For example, a limb scanner such as the PIXSYS Optical Scanner used to develop three-dimensional models for artificial limbs may be used.

Figure 7:
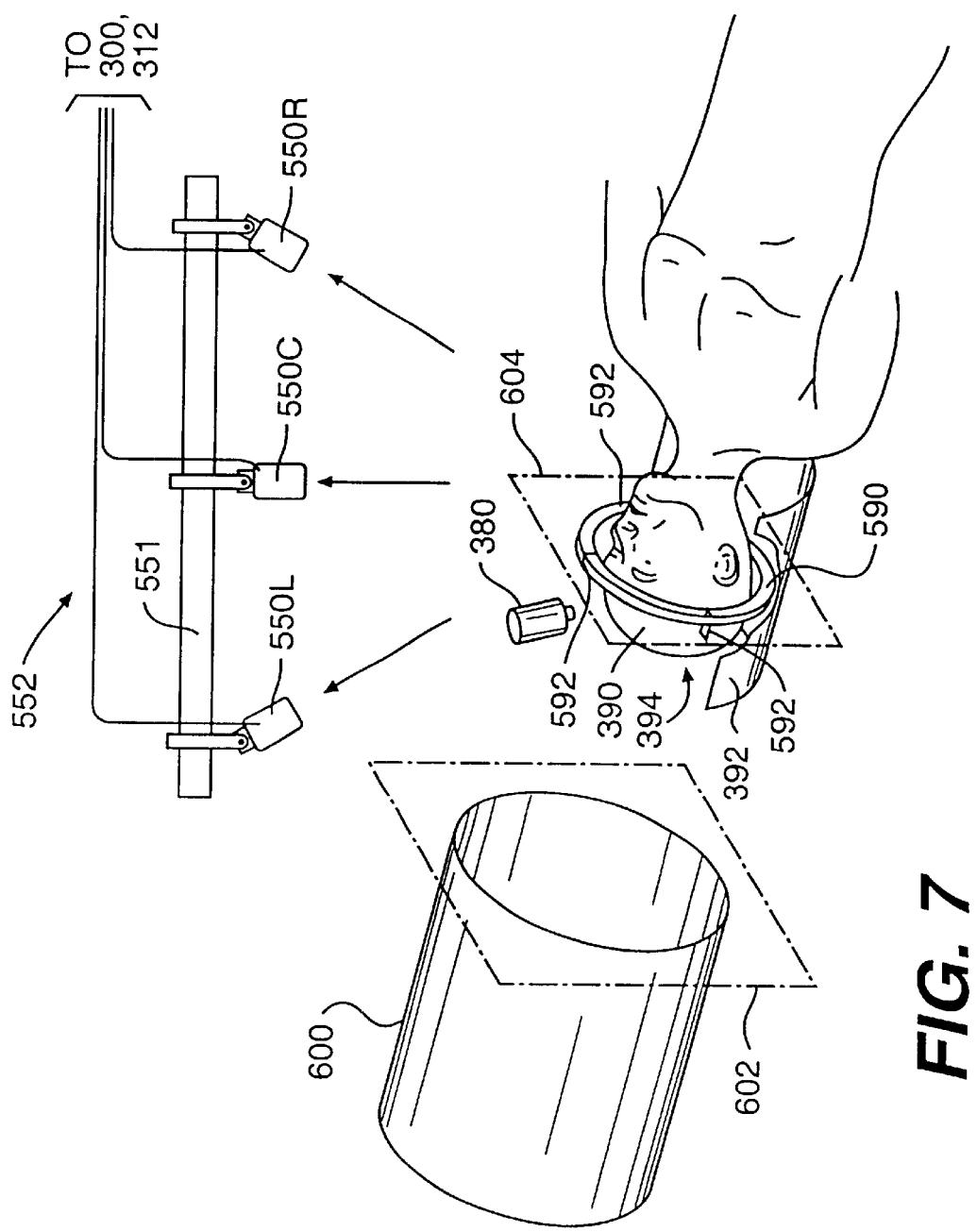
FIG. 7 illustrates the orientation of the base ring with a scanning plane for relating the position of a probe with a scanned image or for interrelating the scanned images of different scanning technologies which correspond to a common position in the head according to one system of the invention.

During the preoperative scanning process, when the cross sectional scanned images of the patient's head 394 are created, head 394 is fastened securely in a cushioned cradle 392 with surgical straps (not shown). If the contour of forehead 390 appears in the scan images, then computer 396 employs forehead fitting software 398 to derive the forehead contour from the scan images and to database the scan images as a function of the forehead contour in memory 320. If the scan images do not show the forehead 390, then (as shown in FIG. 7) head 394 is firmly clamped in fixed relation with a reference source, such as a ring 590, having emitters 592 thereon. Optical scanner 380 is then used to determine the position of the forehead contour relative to ring 590 (as more fully described below). Because the position of the scan images relative to ring 590 is known from the scanning procedure, the position of the scan images relative to the forehead contour is known. This information is then databased in memory 320 and used during surgery to relate the position of probe 542 to the scan images.

Forehead scanning with optical scanner 380 is accomplished in the following way. During preoperative scanning, head 394 is rigidly attached to ring 590 in FIG. 7. This attachment may be accomplished with a base ring (not shown) such as ring 120 in FIG. 3B. Under the control of 3D digitizer 312, scanner 380 emits an infrared laser beam which bounces off a single point on forehead 390 and is detected by array 552. Computer 396 determines the position in space of this first point on forehead 390, such as by triangulation. Next, emitters 592 on ring 590 are energized sequentially. Array 552 detects these emissions and computer 396 determines the relation between the first detected position on forehead 390 and the position of ring 590. This process is repeated many times, with scanner 380 tracing a path across forehead 390. All of the data comprising the position of each point of reflection from forehead 390 and the related position of ring 590 is input into forehead fitting software 398 of computer 396. Computer 396 thereby determines the contour of forehead 390 and, thus, the position of the forehead contour relative to ring 590. Forehead fitting software 398 may be any off-the-shelf or custom software which graphs a set of points so that a curve defining the contour of the forehead can be calculated. Computer 396 then outputs data relating the position of the forehead contour with the position of ring 590 to translational software 318 of computer 314. During scanning, the position of the scan images relative to ring 590 is known so that the position of the scan images relative to the forehead contour is also known. Accordingly, the scan images are stored in memory 320 as a function of the forehead contour.

Prior to surgery, head 394 is clamped with a mechanism such as the Mayfield clamp 570 shown in FIG. 4A for maintaining head 394 in rigid position. Reference bar 548 is rigidly attached to clamp 570 with emitters 545 in line of sight with array 552. Optical scanner 380 next scans the forehead to determine the position of the forehead contour relative to bar 548. The forehead contour derived from this second optical scanning is matched to the forehead contour stored for the scanned images in memory 320 so that the current position of bar 548 with respect to the scanned images is known. The forehead contour matching between the stored forehead contour and the forehead contour derived from the second optical scanning is accomplished using the well known Pellazari Chen algorithm or any other suitable surface matching algorithm. Bar 548 used during surgery includes emitters 545 which communicate with array 552 to establish the position of bar 548. Since the position of probe 542 relative to bar 548 is known (because of communication via emitters 540 and 545 and array 552) and since the position of bar 548 relative to the scanned images is known, the position of probe 542 relative to the scanned images is known. Accordingly, a scanned image corresponding to the position of tip 541 of probe 542 is generated and displayed.

One advantage of using either optical scanner 380 or surgical pins 307 in establishing a reference is that the reference ring, such as ring 120, is removed after preoperative scanning and before surgery. This is advantageous because the patient can not be intubated while ring 120 is attached to the skull. In the prior art, where ring 120 can not be removed during the time between preoperative scanning and surgery, the patient must be intubated (and therefore anesthetized) prior to preoperative scanning. Thus, by using the contour of forehead 390 to define the reference point, the preoperative scanning is performed without the need for intubation and the anesthesia accompanying it. This is particularly advantageous during PET, MEG and any other type of functional scanning where the patient must be conscious to elicit behavior during scanning. It is also advantageous during any form of scanning where the medical equipment for providing intubation and anesthetic would otherwise interfere with the scanning technology, such as MRI scanning.

In summary, when CT scanning is used, the patient lies with the head held in place on a CT table during the preoperative scanning process. The scans are organized in memory 320 according to the forehead contour appearing in the scans. Prior to surgery, the patient's head 394 is rigidly held in a Mayfield clamp or similar clamp on which reference bar 548 is mounted. Optical scanner 380 is then used to determine the patient's forehead contour relative to bar 548. Since the position of the scan images relative to the forehead contour is already known, the position of bar 548 relative to the scan images is known. During surgery, the surgeon positions probe 542 in the position desired within head 394. Emitters 540 of probe 542 and emitters 545 of bar 548 are then energized so that the position of probe tip 541 relative to bar 548 and, therefore, relative to the scan images is known. This is accomplished through the translational software 318 which converts the probe coordinate system $(X_2, Y_2, Z_2)$ into the scanned image coordinate system $(X_0, Y_0, Z_0)$ so that the image corresponding to the position of probe tip 541 can be generated and displayed.

Further summarizing, when MRI, PET or MEG scanning is used, the patient lies on an MRI, PET or MEG table with head 394 rigidly attached to ring 590. Optical scanner 380 then scans forehead 390 to determine the position of the forehead contour relative to ring 590. The MRI, PET or MEG scanning is then performed and the scan images are produced in known relation to the position of ring 590 and, therefore, in known relation to the forehead contour. The scans are organized in memory 320 according to the forehead contour. Prior to surgery, head 394 is rigidly held in a Mayfield clamp or similar clamp on which reference bar 548 is mounted. Optical scanner 380 is then used to determine the patient's forehead contour relative to bar 548. Since the position of the scan images relative to the forehead contour is already known, the position of bar 548 relative to the scan images is known. During surgery, the surgeon positions probe 542 in the position desired within head 394. Emitters 540 of probe 542 and emitters 545 of bar 548 are then energized so that the position of probe tip 541 relative to bar 548 and, therefore, relative to the scan images is known. This is accomplished through translational software 318 which converts the probe coordinate system $(X_2, Y_2, Z_2)$ into the scanned image coordinate system $(X_0, Y_0, Z_0)$ so that the image corresponding to the position of probe tip 541 can be generated and displayed.

Referring to FIG. 5, a flow chart of the operation of translational software 318 is shown as it is used with the apparatus of FIG. 3B. Initially, the surgeon locates probe 542 in the position which is to be determined. (If ring 306 is not being used to identify the location of the reference plane, the initial step is for the surgeon to use the reference mode of 3D digitizer 312 to identify the reference plane by locating probe tip 541 at several points in the plane.) The system then initializes at a step 400 so that translational software 318 opens a window menu at a step 402 of a multitasking program such as DESQ VIEW distributed by Quarterdeck Office Systems of Santa Monica, Calif. Such software permits simultaneous execution of multiple software programs. In general, once a program is selected for actuation, it continues to run either in the foreground or in the background until deactuated.

Translational software 318 continues initializing by selecting stereotactic imaging system 324 through stereotactic image display software 322 and actuating stereotactic imaging system 324 in the foreground by opening the stereotactic window at a step 404. Thereafter, translational software 318 returns to the window menu at a step 406 moving stereotactic image display software 322 to the background and selects the digitizer window at a step 408 to actuate digitizer 312 in the foreground. Computer 314 is then ready to be actuated by the foot switch.

The surgeon then actuates a foot pedal or other switch which indicates that the system should perform a computation. Actuation of the foot switch is essentially the beginning of a start step 410. Upon actuation, if sound transducers 360 and 370 and microphones 350 of FIG. 3B are being used, digitizer 312 initiates calibration through temperature compensation emitter 304 to determine the velocity of the sound waves in the air, energizes emitters 370 of ring 306 to locate the reference plane and energizes emitters 360 of probe 302 to locate the position of probe tip 301. The signals detected by microphone array 300 are digitized so that SAR program 316 determines the coordinates of tip 301. At a step 412, translational software 318 selects the coordinates from SAR program 316.

Next, the window menu is again accessed at a step 414 and the window menu switches stereotactic image system software 322 to the foreground at a step 416 to specifically control the operation of stereotactic imaging system 324. At this point, translational software 318 issues an F1 command to stereotactic image display software 322 which in turn prepares stereotactic imaging system 324 to accept coordinates. At a step 420, the window menu is again selected so that at a step 422 computer 314 switches the digitizer window into the foreground. At a step 424, the digitizer window menu is accessed and coordinate translation is selected. At a step 426, digitizer 312 begins calculating the coordinates and at a step 428 the coordinate calculation is ended. Translational software 318 then returns to the digitizer window menu at a step 430, switches windows to place stereotactic image system software 322 in the foreground at a step 432 to prepare it for receiving the coordinates and again returns to the main window menu at a step 434. Finally, the coordinate information is translated, including any necessary manipulation, and transferred to stereotactic image display software 322 at a step 436 which actuates stereotactic imaging system 324 to generate the particular image from memory 320 and display it on the high resolution display 326. Stereotactic image display software 322 instructs stereotactic imaging system 324 to display a cursor on display 326 at the coordinates which corresponds to the position of probe tip 301. Thereafter, computer 314 is in a standby mode until the foot switch of the surgeon is again actuated to execute translational software 318 beginning with the start step 410.

The translation that occurs in step 436 depends on the position of the probe coordinate system relative to the scanned image coordinate system and the units of measure. The systems are preferably coaxial and the units of measure the same so that algebraic adjustment is unnecessary. However, it is contemplated that the coordinates systems may not be coaxial, in which case translation would require arithmetic and/or trigonometric calculations. Also, the sequence, e.g., $(X_2, Y_2, Z_2)$, in which the coordinates are generated by the digitizer 312 may be different than the sequence, e.g., $(X_0, Y_0, Z_0)$, in which the stereotactic image system software 322 receives coordinates. Therefore, the sequence in which the coordinates are transferred may have to be reordered.

Those skilled in the art will recognize that the above computer programming could be accomplished in a number of other ways without departing from the scope of the invention. As one example, and apart from the use of multitasking programs and their associated windows and menus, a personal computer could be directly programmed to calculate the coordinates of the position of probe tip 301 for use in generating the scan image corresponding to the position of tip 301 from the data stored in memory 320.

The steps performed by translational software 318 for the system of FIG. 4A are similar to those described above for the system of FIG. 3B with the following exceptions. First, the system of FIG. 4A does not require a calibration emitter such as emitter 304 in FIG. 3B so that the corresponding step is skipped in the software for FIG. 4A. Further, infrared emitters 540 and 545 are used in place of sound emitters 360 and 370 for determining the position of probe tip 541 and bar 548. As above, the various positions of the emitters are determined based on the angle of the view of detectors 550 to each of emitters 540 and 545. The angle is known from knowing which pixel within each of detectors 550 detects the infrared light. Still further, when the optical scanner 380 is used, translational software 318 for the system of FIG. 4A includes additional steps for operating optical scanner 380 through multiplexer 310 to scan a series of infrared laser beams across forehead 390 for detection by detectors 550. This data is received by digitizer 312 and passed to computer 396 so that the forehead contour can be determined through software 398. Data identifying the forehead contour is then passed back to translational software 318 for use as a reference.

Figure 6B:
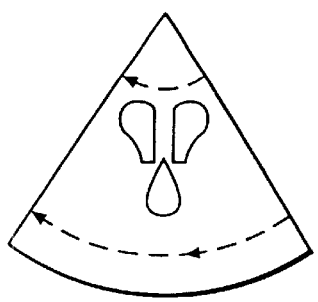
FIGS. 6B and 6C illustrate ultrasound and scanned images, respectively.
Figure 6C:
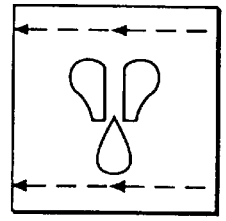
Figure 6A:
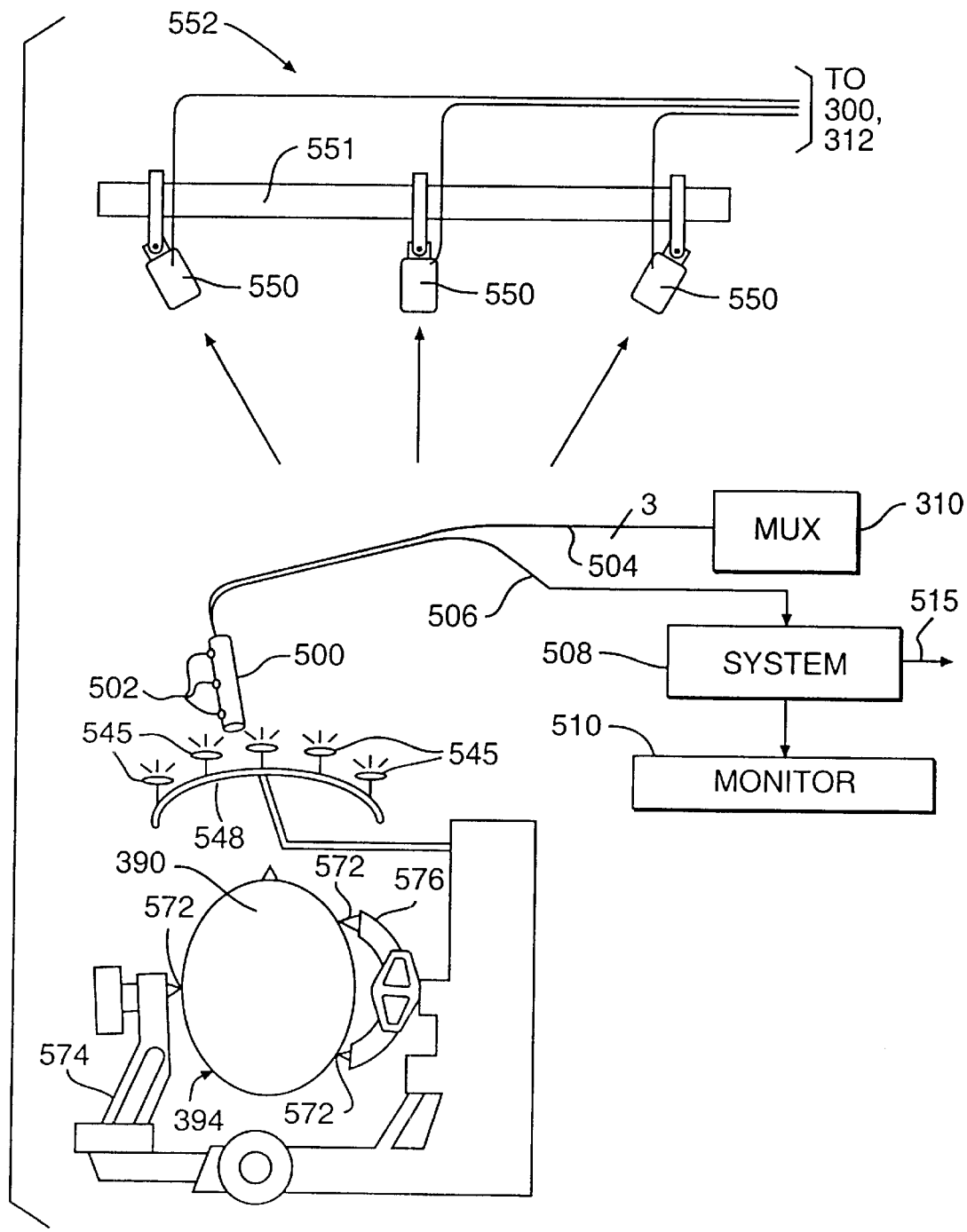
FIG. 6A is a perspective schematic diagram of a detector array, reference bar, clamp and ultrasound probe according to one system of the invention.

Referring to FIG. 6A, a system of the present invention employing an ultrasound localizer is illustrated. The ultrasound system includes a mechanism such as a Mayfield head clamp 570 for maintaining head 394 in rigid position. Reference bar 548 is rigidly attached to clamp 570 as above with emitters 540 in line of sight with array 552. The forehead contour is determined by optical scanning using optical scanner 380 and array 552 of detectors 550 as shown in FIG. 4A and as more fully described above. The ultrasound system also includes an ultrasound probe 500 which may be used in the operating room to scan the brain. Ultrasound probe 500 includes a plurality of at least three noncolinear emitters 502 which are energized via a line 504 by multiplexer 310. The signal emitted by emitters 502 is received by array 552 to determine the position of the body of ultrasound probe 500 relative to the position of forehead 390. This is accomplished through translational software 318 which controls digitizer 312 and multiplexer 310 to energize emitters 502 in a predetermined sequence to determine the position of the body of probe 500. This is the same technique used above in FIGS. 3B and 4A for determining the position of probes 302 and 542 and of rings 306 and 548. Ultrasound probe 500 is also connected via a line 506 to a system 508 of known construction which analyzes the ultrasound scanning and provides the analyzed information to a monitor 510 which displays the ultrasound image. Since array 552 can determine the position of the body of ultrasound probe 500 at any point in time, via digitizer 312, the particular plane of the image displayed on monitor 510 is known.

An ultrasound image is illustrated by way of example in FIG. 6B. Because the plane of the ultrasound scan image is known, the surgeon can signal stereotactic imaging system 324 to generate a scan image from a different scanning technology on display 326 which corresponds to the ultrasound image. FIG. 6C illustrates such a corresponding image. Alternatively, system 508 may be linked to stereotactic imaging system 324 directly via a data link 515 to communicate the position of the scan plane for the image shown on monitor 510 so that stereotactic imaging system 324 can automatically generate and display the corresponding scanned image for a different scanning technology on display 326. As a result, the image from the ultrasound system, as illustrated on monitor 510, is shown on one monitor and may be compared to a corresponding image obtained from CT, MRI, PET, MEG or some other type of preoperative scanning. The cross section through the three dimensional data set as developed by the ultrasound system is determined by a high speed graphics system 508, such as manufactured by Silicon Graphics. This allows for better interpretation of the ultrasound scans as the anatomy from the MRI, CT, PET or MEG scans can be seen directly. Furthermore, the ultrasound system allows scanning in the operating room. Since the brain tissue is elastic and the position of various tissue may change from time to time, use of an ultrasound scan in the operating room permits a more definite localization of various brain tissues. For clarity, ultrasound probe 500 is shown in FIG. 6A as spaced away from head 394. Usually, ultrasound probe 500 is positioned in contact with the skull during use. The probe may also be affixed to the skull during surgery for continual monitoring of the position of the brain.

FIG. 7 shows a system of the present invention for correlating the scan images from different scanning technologies. A scanner 600 represents any of the several scanning technologies currently available (e.g. CT, MRI, PET, MEG) and is intended to include any other scanning technologies that may be developed. Scanner 600 scans head 394 in a plane 602. Plane 602 is usually defined visually by an array of light beams. If the pertinent scanning technology reveals the position of the forehead contour in the scan images, then computer 396 employs forehead fitting software 398 to derive the forehead contour from the scan images. Computer 396 organizes the scan images as a function of the forehead contour for storage in memory 320.

If the pertinent scanning technology does not reveal the position of the forehead contour in the scan images, then ring 590 is rigidly attached to head 394. The optical scanner 380 is used prior to scanning to relate the position of the forehead contour relative to ring 590 (as described in the text accompanying FIG. 4A). Ring 590 lies in a plane 604. During scanning, planes 602 and 604 are preferably maintained in parallel relation by initially aligning ring 590 coplanar with the visual array of light beams defining plane 602. However, it is not necessary to initially align ring 590 coplanar with scan plane 602. As long as the relative relationship in space between ring 590 and plane 602 is known and that relationship is maintained during the scanning, the orientation of the forehead relative to the scan plane can be calculated. Since ring 590 will appear in at least one scan and since the position of one scan within a group is known with respect to the other scans in the group, the respective positions of the scans relative to ring 590 is known. Since the position of the forehead contour relative to ring 590 was determined by scanning the forehead with scanner 380, the position of the forehead contour relative to the scan images is known. Computer 396 now employs forehead fitting software 398 to organize the scan images as a function of the forehead contour. This information is databased in memory 320. The forehead contour is then used to relate the scan images of one technology such as PET to the scan images produced from any other technology such as CT, MRI, or MEG.

When the scan images from several technologies are available, it is contemplated within the scope of the invention to use a like number of displays to display each of the scan images corresponding to the position of the probe 302 or 542, or to use a lesser number of displays, each showing multiple scan images. Likewise, it is contemplated that a scan image from one technology may be used as a reference in locating corresponding scan images from other technologies. Finally, while this disclosure broadly describes the use of the invention for scanning the patient's head, it is contemplated within the scope of the invention to use the invention for scanning and analyzing other portions of the body of the patient.

Figure 8:
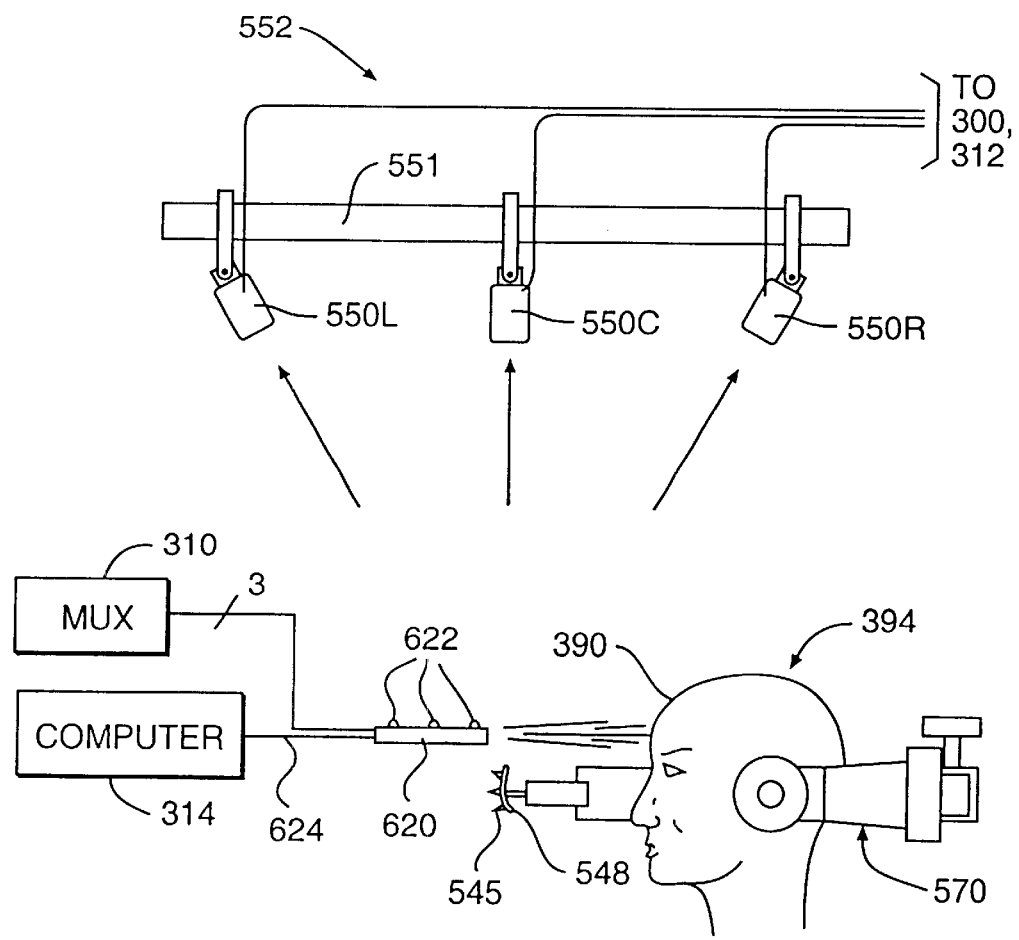
FIG. 8 illustrates the use of a remote depth finder for determining the contour of a forehead.

FIG. 8 shows a laser depth finder 620 for use in scanning the forehead contour when the line of sight between optical scanner 380 and array 552 in FIG. 4A is blocked. FIG. 8 includes a Mayfield clamp 570 for holding head 394 in fixed relation to a reference bar 548 having emitters 545 thereon. Depth finder 620 may be any of the laser based depth finders commonly available which are accurate to within the required tolerances. At least three emitters 622 are affixed to depth finder 620. Emitters 622 are controlled via multiplexer 310 so that computer 314 can determine the position of depth finder 620 in addition to the position of bar 548. In operation, depth finder 620 emits an infrared laser beam which is reflected off of forehead 390 and detected by a detector within depth finder 620. The circuitry inside depth finder 620 calculates the distance between the illuminated point on forehead 390 and a reference point on depth finder 620 and outputs a signal corresponding to the calculated distance via a line 624 to computer 314. Computer 314 then sequentially fires emitters 545 and 622 via multiplexer 310 to determine the positions of bar 548 and depth finder 620. Accordingly, at the end of this first cycle, one point of the forehead contour can be calculated. This cycle is repeated a number of times until computer 314 has obtained sufficient points to map the forehead contour.

Figure 9:
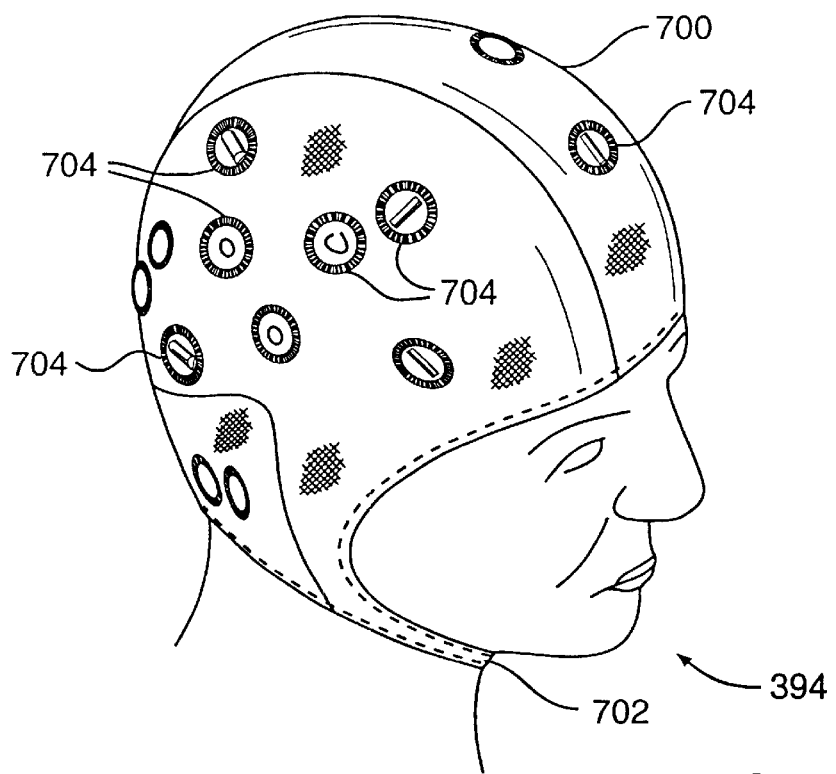
FIGS. 9 through 11 illustrate apparatus including a cap and grommets for holding radiopaque markers during scanning.
Figure 10:
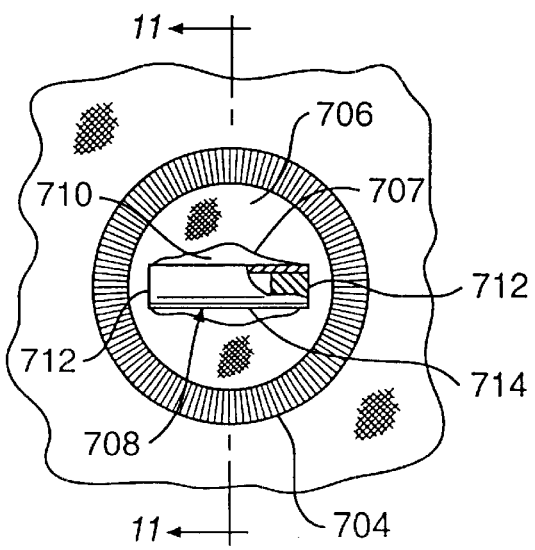
Figure 11:
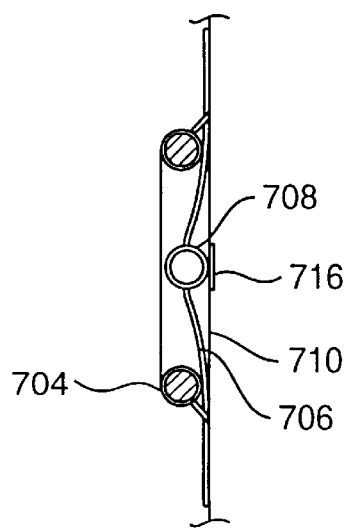

FIGS. 9–11 show an alternative system for registering scan images with the surgical space. FIG. 9 includes a cap 700 which fits snugly over head 394. Cap 700 is secured by an adjustable strap 702. In use, there should be no relative movement between cap 700 and head 394. A plurality of grommets 704 are sewn into cap 700 at regular intervals. FIG. 10 shows one such grommet in greater detail and FIG. 11 shows the cross-section through FIG. 10 at the indicated line. As can be seen in these figures, grommets 704 encircle and thereby reinforce fabric 706 of cap 700. A hole 707 centrally positioned within each grommet 704 is cut into fabric 706 and provides space for supporting a marker 708 and also provides access to underlying skin 710 on head 394.

Fabric 706 is preferably elastic in nature. The hole 707 in fabric 706 is smaller than the external dimensions of marker 708 so that fabric 706 is stretched slightly to hold marker 708. For example, hole 707 may be a slit within fabric 706.

Markers 708 include an internal reservoir filled with a radiopaque substance which is detected by the scanner during scanning and which appears on the scan images. For example, the markers for CT scanning are filled with omnipaque, the markers for MRI scanning are filled with gadolinium, and the markers for PET scanning are filled with a radioactive tracer. The capacity of the reservoirs in markers 708 is different for the different scanning technologies because each scanning technology has a different resolution. However, markers 708 preferably have a uniform external dimension so that the same cap 700 can be used with any of the different types of scanners and related markers. Markers 708 are easily attached within and removed from fabric 706 to allow quick access for marking skin 710 underneath. This is also helpful for patients who are undergoing more than one scanning procedure using different scanning technologies. When multiple scanning technologies are used, the markers for the different technologies may be attached to fabric 706 within the same grommets 704 so that the images produced by the different scanners all show markers 708 in the same places. Markers 708 preferably consist of clear plastic material such as polyethylene tubing filled with a contrast medium 710 in the center and sealed at both ends with epoxy 712. Markers 708 can be either prefilled and sealed with suitable contrast medium or fillable by needle puncture with the contrast medium.

For cranial surgery, cap 700 is preferably made of fabric consisting of 85% Dupont Antron Nylon and 15% Lycra Spandex. Although one size may fit most patients, the cap 700 can be sized or shaped to specific patients. Three-quarter inch grommets 704 are sewn at routine intervals over the entirety of the cap. For surgery on other parts of the body, a flexible material is used which fits snugly like an ace wrap bandage. Again, grommets 704 are sewn every one or two inches. As with cap 700, there is a hole in the fabric 706 in the center of each grommet for holding markers 708.

In use, the patient is instructed to wash his/her hair and to not apply any hair spray, lotion, or other materials prior to scanning in order to provide as oil-free of a surface as is possible. After cap 700 is snugly fit over head 394 and secured with chin strap 702, the surgeon selects at least three (preferably more) grommets 704 which will be used to hold markers 708. As accuracy of three point registration increases with greater separation of markers, markers 708 are preferably placed over the largest area available to insure a low margin of error. If surgery is planned, hair surrounding the operative area can be clipped or left in place as desired by the surgeon. A small amount of hair is clipped or displaced around the area where markers 708 will be used to allow the positioning of markers 708 close to skin 710. Skin 710 is marked with indelible ink 716 through the holes in fabric 706 of the grommets 704 in which a marker 708 is to be attached. Markers 708 are then attached to said fabric. During this time, the surgeon carefully checks to insure that each marker 708 is positioned adjacent to and directly over the ink mark 716 on skin 710. Ink mark 716 is preferably positioned in the center of the hole in fabric 706. The patient is then positioned on the scanning table and head 394 is scanned. After scanning, markers 708 are removed. During removal of the markers, the surgeon carefully checks to see that each marker did not move during scanning by checking to see that each is still positioned adjacent to and directly over the corresponding ink mark 716. Further, the ink marks should appear in the center of the holes in fabric 706. If a marker is no longer in position adjacent the related ink mark and/or if the ink mark is not in the center of the hole, it indicates that movement of the marker has occurred some time during scanning. Accordingly, the particular ink mark 716 and its corresponding marker 708 are not used during the subsequent registration process where the scan images are registered with the surgical space. If enough of the markers have moved from their positions so that the position of three of the markers can not be confirmed, then the scan is repeated.

If scanning occurs immediately prior to surgery, the indelible ink marks 716 may need no protection from the possibility of smudging or accidental removal. The patient is issued a paper cap to wear until the time of surgery and is instructed not to remove or interfere with the ink marks. If there will be a delay between scanning and surgery, there are several ways to assure the integrity of the indelible marks. For example, benzoin can be applied to the area surrounding the indelible mark and allowed to dry. A strip of three-quarter inch transparent tape is then applied to the area. Collodium may also be used in a similar way to protect the marks.

After the integrity of at least three ink marks 716 has been confirmed, a three point solution utilizing directional cosines from two frames of reference enables the surgeon to register the surgical space with the scan images. If the integrity of more than three marks 716 is confirmed, the additional marks can be used for redundancy to insure that the registration was properly performed. The registration process can be accomplished using the apparatus shown in FIGS. 4A and 3A. In particular, following scanning with cap 700 and markers 708, computer 314 processes and stores the scan images in memory 320 as a function of the markers 708 which appear in the scan images using similar techniques as those described above. Prior to surgery, head 394 is clamped in clamp 394. The tip 541 of probe 542 is then touched on each of the ink marks 716 on skin 710 of head 394 while the emitters 540 and 545 are energized. Because computer 314 now knows the position of each of ink marks 716 relative to reference bar 548, it can determine the position of the scan images relative to reference bar 548. During surgery, as described above, emitters 540 and 545 enable computer 314 to also know the position of probe tip 541 relative to reference bar 548. Accordingly, computer 314 knows the position of probe tip 541 relative to the scan images. Computer 314 then generates a scan image corresponding to the position of tip 541. The generated image is displayed on display 326.

As can be seen, there are many advantages of using cap 700 and markers 708 to register the scan images to the surgical space. For example, and unlike the placement of reference pins 307 in FIG. 3D, the placement of markers 708 does not cause any pain to the patient. This is because markers 708 are noninvasive and do not require the skin to be broken when they are used. Accordingly, redundant markers are used which provide greater accuracy and which insure in most cases that at least three of the markers will be useable for registering the scan images. Another advantage is that routine scans can be taken with markers 708 in place. If the initial scan locates a lesion that requires surgery, the position of the scan images relative to markers 708 is known and the same scan images can be used during surgery. Because of the pain involved in implanting reference pins 307, however, they would rarely be used during routine scanning. If a lesion is found during such routine scanning, the entire scan has to be retaken again after pins 307 are implanted. Yet another advantage of using markers 708 during scanning is that they are removed prior to surgery and so they do not need to be sterilized. Thus, the difficulty otherwise encountered in trying to sterilize such markers is avoided.

For surgery on parts of the body other than the head, a material with grommets 704 sewn at regular intervals is wrapped once around the part being examined and attached with fasteners that do not distort the image produced. The material is applied snugly, like an ace wrap, with grommets every one to two inches. Alternatively, the fabric can be made into a corset like structure, with the salient feature being reinforcement with grommets that allow holes to be made in the fabric without weakening it, and that also allow placement of markers 708. As with cap 700, the skin is marked with indelible ink 716 under each marker. After scanning, marker. 708 is removed and the skin mark 716 is checked to insure that the marker has not moved.

Those skilled in the art will recognize that apparatus other than cap 700 could be used for positioning markers 708 within the scope of the invention. For example, markers 708 can be held in place adjacent an ink mark 716 using tape. Such transparent tape has been found to be particularly effective in positioning markers on the forehead and other hairless areas. Further, apparatus other than grommets 704 and fabric 706 can be used to hold markers 708 within cap 700. Such other apparatus includes any of the commonly found fasteners and mechanical fixtures capable of holding relatively small objects.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. A system for determining the position of a probe relative to a body of a patient, said system comprising:
    a receiver configured to receive signals;
    a reference fixed in relation to the body, the reference in a line of sight with the receiver and capable of passing a signal representing the position of the reference to the receiver;
    a memory having stored images of the body, the images including reference images correlatable to the reference;
    a probe in a line of sight with the receiver and capable of passing a signal representing the position of the probe to the receiver;
    a processor in communication with the receiver and the memory, wherein the processor is configured to determine the position of the reference relative to the receiver, to determine the position of the probe relative to the reference and to determine the position of the probe relative to the body, and, in response to such determined positions, to translate the position of the probe relative to the body to the position of the probe relative to the body in the images of the body; and
    a display of the images of the translated position of the probe relative to the body.

2. The system of claim 1, wherein the reference includes pins fixed in relation to the body.

3. The system of claim 1, wherein the reference includes a ring fixed in relation to the body.

4. The system of claim 1, wherein the probe is an imaging probe capable of taking scan images of the body.

5. The system of claim 1, wherein the probe is surgical forceps.

6. The system of claim 1 wherein the probe comprises an imaging probe configured to scan the body part providing scan images of the body part and capable of passing a signal representing the position of the imaging probe relative to the receiver.

7. A system for determining a position of an instrument relative to a body of a patient, said system comprising:
    a base fixed in relation to the body and a base signal associated with the base;
    a memory having stored images of the body, the images including reference images correlatable to the base;
    an instrument and an instrument signal associated with the instrument;
    a digitizer configured to determine the position of the base and the instrument based on the base signal and the instrument signal;
    a computer in communication with the digitizer and the memory, wherein the computer is configured to determine the position of the body in the images of the body, to determine the position of the instrument relative to the base, to determine the position of the instrument relative to the body, and in response to such determined positions, to translate the position of the instrument relative to the body to the position of the instrument relative to the body in the images of the body; and
    a display of the images of the translated position of the instrument to the body.

8. The system of claim 7, wherein the base includes pins fixed in relation to the body.

9. The system of claim 7, wherein the base includes a ring fixed in relation to the body.

10. The system of claim 7, wherein the instrument is an imaging probe capable of taking scan images of the body.

11. The system of claim 7, wherein the instrument is surgical forceps.

12. The system of claim 7, wherein the probe comprises an imaging probe configured to scan the body providing scan images of the body and having a probe signal associated therewith.

13. A system for determining a position of an instrument relative to a body of a patient, said system comprising:
    a base fixed in relation to the body and a base signal associated with the base;
    a memory having stored images of the body, the images including reference images correlatable to the base;
    an instrument and an instrument signal associated with the instrument;
    a detector detecting the base signal and the instrument signal;
    a computer in communication with the detector and the memory, the computer configured to determine the position of the body in the images of the body, to determine the position of the instrument relative to the base, to determine the position of the instrument relative to the body, and in response to such determined positions, to translate the position of the instrument relative to the body to the position of the instrument relative to the body in the images of the body; and
    a display of the images of the translated position of the instrument to the body.

14. The system of claim 13, wherein the base includes pins fixed in relation to the body.

15. The system of claim 13, wherein the base includes a ring fixed in relation to the body.

16. The system of claim 13, wherein the instrument is an imaging probe capable of taking scan images of the body.

17. The system of claim 13, wherein the instrument is surgical forceps.

18. The system of claim 13, wherein the probe comprises an imaging probe configured to scan the body providing scan images of the body and having a probe signal associated therewith.

19. The system of claim 13, further including a digitizer which communicates with the computer, the digitizer being capable of determining the position of the base and the instrument based on the base and the instrument signals.

20. A system for determining a position of an instrument relative to a body of a patient, said system comprising:
   a base fixed in relation to the body, the base energizable to provide signals representing the position of the base;
   a memory having stored images of the body, the images including reference images correlatable to the base;
   an instrument, the instrument being energizable to provide signals representing the position of the instrument;
   an array of detectors, the detectors detecting the signals representing the position of the base and the instrument;
   a processor in communications with the array and the memory, wherein the processor is configured to determine the position of the body in the images of the body, to determine the position of the base and the instrument based on the signals detected by the array, to determine the position of the instrument relative to the base, and to determine the position of the instrument relative to the body; and
   a display of the images of the translated position of the instrument to the body.

21. The system of claim 20, further including a digitizer which communicates with the processor, the digitizer being configured to determine the position of the base and the instrument based on the signals detected by the array.

22. The system of claim 20, wherein the base includes pins fixed in relation to the body.

23. The system of claim 20, wherein the base includes a ring fixed in relation to the body.

24. The system of claim 20, wherein the instrument is an imaging probe capable of taking scan images of the body.

25. The system of claim 20, wherein the instrument is surgical forceps.

26. The system of claim 20, wherein the probe comprises an imaging probe configured to scan the body providing scan images of the body and being energizable to provide signals representing the position of the imaging probe.

27. A system for determining a position of an instrument relative to the body of a patient, the system comprising;
   a base fixed in a known relationship to the body, the base configured to provide a signal representing the position of the body part;
   a trackable instrument configured to provide a signal representing the position of the instrument;
   an array configured to detect signals provided by the base and the instrument;
   a processor, including a memory containing scan images of the body, in communication with the array, wherein the processor is configured to determine the position of the instrument relative to the body in the images of the body; and
   a display for displaying images of the instrument relative to the body.

28. The system of claim 27, wherein the base includes pins fixed in relation to the body.

29. They system of claim 27, wherein the base includes a ring fixed in relation to the body.

30. The system of claim 27, wherein the instrument is an imaging probe capable of taking scan images of the body.

31. The system of claim 27, wherein the instrument is surgical forceps.

32. The system of claim 27, wherein the probe comprises a trackable imaging probe configured to scan the body providing scan images of the body and to provide a signal representing the position of the imaging probe.

33. A method for determining a position of an instrument relative to a body of a patient in a coordinate system, the method comprising:
   fixing a reference base in a known relation to the body of the patient;
   energizing the base to provide signals representing the position of the base in the coordinate system;
   energizing an instrument to provide signals representing the position of the instrument in the coordinate system;
   detecting the signals provided by the base and the instrument with an array of detectors;
   determining the position of the base and the instrument in the coordinate system based on the signals detected by the array of detectors;
   determining the position of the body of the patient in the coordinate system based on the known position of the base relative to the body of the patient and the position of the base in the coordinate system; and
   determining the position of the instrument relative to the body of the patient based on the determined positions of the instrument and the body of the patient in the coordinate system.

34. The method according to claim 33, further comprising the steps of
   determining the position of the body in previously scanned images of the body; translating the position of the instrument relative to the body to the position of the instrument relative to the body in the images of the body; and displaying images of the translated position of the instrument relative to the body.

35. The method of claim 34 wherein the probe comprises an imaging probe and further comprising the steps of:
   energizing the imaging probe positioned relative to the body of a patient to provide signals representing the position of the imaging probe in the coordinate system;
   scanning the body using the imaging probe creating a scan image of the body;
   detecting the signals provided from the imaging probe;
   determining the position of the imaging probe in the coordinate system based on the signals detected;
   determining the position of the body part in the scan image of the body part based on the position of the imaging probe relative to the body part;
   displaying an image of the body part which corresponds to the position of the imaging probe in the scan image.

36. The method of claim 35, further including the steps of determining the position of the instrument in the scan image of the body part based on the position of the instrument relative to the body part, and displaying an image of the body part which correspond to the position of the instrument in the scan image.

37. A method for indicating a location of an instrument relative to the body part of a patient comprising the steps of:

positioning an instrument relative to a body part of a patient, the instrument capable of providing signals and the body part having reference points capable of providing signals;

providing signals from the instrument to indicate the position of the instrument;

providing signals from the reference points to indicate the position of the reference points and the body part;

detecting the signals provided from the instrument and reference points;

processing the detected signals from the instrument and from the reference points to determine the position of the instrument relative to the body part;

retrieving a previously scanned image of the body part;

determining the position of the body part in the previously scanned image of the body part;

correlating the position of the instrument relative to the body part to the image of the body part; and displaying an image of the instrument relative to the body part in the image of the body part.

38. The method of claim 37 further comprising the steps of:

positioning an imaging probe relative to the body of a patient, the imaging probe capable of providing signals;

scanning the body part using the imaging probe creating a scan image of the body part;

providing signals from the imaging probe;

detecting the signals provided from the imaging probe;

processing the detected signals from the imaging probe to determine the position of the imaging probe relative to the body part;

determining the position of the body part in the scan image of the body part based on the position of the imaging probe relative to the body part;

displaying an image of the body part which corresponds to the position of the imaging probe in the scan image.

39. The method of claim 38, further including the steps of determining the position of the instrument in the scan image of the body part based on the position of the instrument relative to the body part, and displaying an image of the body part which correspond to the position of the instrument in the scan image.

40. The method of claim 37, wherein the instrument is an imaging probe for taking scan images of the body part.

41. The method of claim 37, wherein the instrument is surgical forceps.

42. A method for indicating the position of a structure within a body of a patient having multiple structures in a coordinate system, the method comprising:

placing a surgical probe at the structure within a body of a patient;

providing signals from the probe to a location remote from the probe representing the position of the probe at the structure in the coordinate system;

identifying the position of the probe in the coordinate system from the signals from the probe;

retrieving a scan image of the body part from a memory storing images of the body part corresponding to the position of the probe at the structure in the coordinate system;

displaying the scan image of the body part corresponding to the position of the probe at the structure in the coordinate system on a display; and displaying on the scan image of the body part an image representing the probe at the structure.

43. The method of claim 42, further comprising determining the boundary of the body part in the retrieved image and displaying the boundary of the body part.

* * * * *